(12) United States Patent
Imura

(10) Patent No.: US 12,351,890 B2
(45) Date of Patent: Jul. 8, 2025

(54) METHOD FOR SYNTHESIZING ZIRCONIUM COMPLEX

(71) Applicant: JFE ENGINEERING CORPORATION, Tokyo (JP)

(72) Inventor: Ryota Imura, Tokyo (JP)

(73) Assignee: JFE ENGINEERING CORPORATION, Tokyo (JP)

( * ) Notice: Subject to any disclaimer, the term of this patent is extended or adjusted under 35 U.S.C. 154(b) by 696 days.

(21) Appl. No.: 17/630,472

(22) PCT Filed: Jun. 25, 2020

(86) PCT No.: PCT/JP2020/025031
§ 371 (c)(1),
(2) Date: Jan. 26, 2022

(87) PCT Pub. No.: WO2021/019983
PCT Pub. Date: Feb. 4, 2021

(65) Prior Publication Data
US 2022/0259698 A1 Aug. 18, 2022

(30) Foreign Application Priority Data
Jul. 30, 2019 (JP) .................. 2019-139778

(51) Int. Cl.
*C07D 255/02* (2006.01)
*A61K 51/04* (2006.01)
(Continued)

(52) U.S. Cl.
CPC ............ *C22B 34/14* (2013.01); *C07D 255/02* (2013.01); *C07D 257/02* (2013.01); *A61K 51/0482* (2013.01)

(58) Field of Classification Search
CPC .... C22B 34/14; C07D 255/02; C07D 257/02; A61K 51/0482
See application file for complete search history.

(56) References Cited

U.S. PATENT DOCUMENTS 10,195,295 B2  2/2019  Buffel et al.
10,501,332 B2  12/2019  Scapens
(Continued)

FOREIGN PATENT DOCUMENTS

CN  101909744 A  12/2010
CN  105939994 A  9/2016
(Continued)

OTHER PUBLICATIONS

Anand, et al. "Zwitterions for impedance spectroscopy: The new buffers in town." Analytica Chimica Acta 1166 (2021): 338547 (Year: 2021).*
(Continued)

*Primary Examiner* — Anthony J Zimmer
*Assistant Examiner* — Eric Scott Sherman
(74) *Attorney, Agent, or Firm* — Rimon P.C.

(57) ABSTRACT

A method for synthesizing a zirconium complex includes: mixing a solvent containing an organic substance having a dipole moment of 3.0 D or more, a chelating agent solution in which a chelating agent containing a structure represented by General Formula (1) or General Formula (2) is dissolved, and zirconium dissolved in an acidic solution, to obtain a mixed solution; and setting the mixed solution at a predetermined temperature or more to synthesize a zirconium complex.

(Continued)

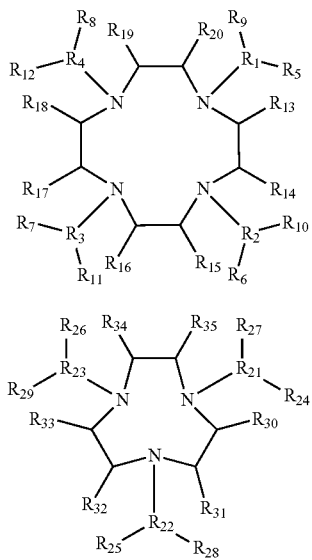

12 Claims, 2 Drawing Sheets

(51) Int. Cl.
*C07D 257/02* (2006.01)
*C22B 34/14* (2006.01)

(56) References Cited

U.S. PATENT DOCUMENTS

| | | |
|---|---|---|
| 2010/0274039 A1 | 10/2010 | Choi et al. |
| 2014/0147381 A1 | 5/2014 | Espenan |
| 2017/0007726 A1 | 1/2017 | Buffel et al. |
| 2018/0319671 A1 | 11/2018 | Scapens |
| 2019/0038785 A1* | 2/2019 | Wadas .............. A61K 51/1093 |
| 2021/0017099 A1 | 1/2021 | Dudkin et al. |

FOREIGN PATENT DOCUMENTS

| | | | | |
|---|---|---|---|---|
| CN | 106075484 | A | 11/2016 | |
| CN | 108473337 | A | 8/2018 | |
| JP | 2018123372 | * | 8/2018 | .............. Y02P 10/20 |
| JP | 2018-123372 | A | 8/2019 | |
| JP | 6665806 | B2 | 3/2020 | |
| WO | 2017/161356 | A1 | 9/2017 | |
| WO | 2019/125982 | A1 | 6/2019 | |

OTHER PUBLICATIONS

International Search Report issued in corresponding International Patent Application No. PCT/JP2020/025031, dated, Sep. 8, 2020, with English translation.
Graves, S.A. et al., "Evaluation of a chloride-based 89Zr isolation strategy using a tributyl phosphate (TBP)-functionalized extraction resin," Nuclear Medicine and Biology, 2018, vol. 64, 65, pp. 1-7.
Taha, M. et al., "Phase behavior and molecular dynamics simulation studies of new aqueous two-phase separation systems induced by HEPES buffer," Journal of Physical Chemistry B, 2013, vol. 117, No. 2, pp. 563-582.
Pandya, D. N. et al., "Zirconium tetraazamacrocycle complexes display extraordinary stability and provide a new strategy for zirconium-89-based radiopharmaceutical development," Chemical Science, 2017, vol. 8, No. 3, pp. 2309-2314.
Extended European Search Report issued in corresponding European Patent Application No. 20846290.3, dated Jun. 28, 2023.
Office Action received in corresponding Chinese patent Application No. 202080092776.4 on Jan. 31, 2024, with a concise statement of relevance and English Translation.
D.N. Pandya et al. "Polyazamacrocycle Ligands Facilitate 89Zr Radiochemistry and Yield 892Zr Complexes with Remarkable Stability", American Chemical Society, Inorganic Chemistry, Nov. 10, 2020, vol. 59, No. 23, pp. 17473-17487.
International Search Report dated Feb. 2, 2021, issued in corresponding International Application No. PCT/JP2020/045605.
Extended European Search Report issued for the corresponding European patent Application No. 20914026.8 on Dec. 20, 2023.
Canadian Office Action issued Sep. 5, 2023, in corresponding Canadian Patent Application No. 3166187.
Australian Office Action issued Apr. 19, 2023, in corresponding Australian Patent Application No. 2020423724.

* cited by examiner

METHOD FOR SYNTHESIZING ZIRCONIUM COMPLEX

CROSS-REFERENCE TO RELATED APPLICATIONS

This application is the U.S. National Phase under 35 U.S.C. § 371 of International Application No. PCT/JP2020/025031, filed on Jun. 25, 2020, which claims the benefit of Japanese Application No. 2019-139778, filed on Jul. 30, 2019, the entire contents of each are hereby incorporated by reference.

FIELD

The present invention relates to a method for synthesizing a zirconium complex, in which a complex of radioactive zirconium such as $^{89}$Zr and a chelating agent is synthesized.

BACKGROUND

It has conventionally been known that radioactive zirconium ($^{89}$Zr) has high resolution and a medium half-life of about 78 hours and is thus a radio isotope effective in medical imaging. As a method for producing radioactive zirconium, a method irradiating an yttrium (Y) target with proton rays is known. In the method of production using proton rays, irradiation for a few hours generates a minute amount of radioactive zirconium in units of a few gigabecquerels (GBq) (a few tens of to a few hundreds of nanograms (ng) in terms of mass) in yttrium in units of a few hundreds of milligrams (mg).

For labeling of metal radioactive nuclides, 1,4,7,10-tetraazacyclododecane-1,4,7,10-tetraacetic acid (DOTA), 1,4,7-triazacyclononane-1,4,7-triacetic acid (NOTA), and similar compounds thereof are widely used as chelating agents. DOTA and NOTA are chelating agents having high versatility forming complexes with almost all metal nuclides such as radioactive cupper (Cu), gallium (Ga), yttrium (Y), indium (In), lutetium (Lu), and actinium (Ac). Formation of a complex of DOTA and zirconium (Zr) has so far been considered to be difficult, but it has been revealed that the complex can be formed by reacting them at a high temperature of about 95° C. (refer to Non Patent Literature 1).

CITATION LIST

Patent Literature

Patent Literature 1: Japanese Patent Application Laid-open No. 2018-123372
Patent Literature 2: Japanese Patent No. 6665806
Non Patent Literature 1: Zirconium tetraazamacrocycle complexes display extraordinary stability and provide a new strategy for zirconium-89-based radiopharmaceutical development, Chem. Sci. 2017, 8, 2309-2314.
Non Patent Literature 2: Evaluation of a chloride-based 89Zr isolation strategy using a tributyl phosphate (TBP)-functionalized extraction resin, Nucl. Bio. and Med., 2018, 64, 1-7.

SUMMARY

Technical Problem

However, to react radioactive zirconium ($^{89}$Zr) and DOTA while ensuring a sufficient radiochemical yield, the concentration of DOTA is required to be higher than $10^{-4}$ mol/L (refer to Non Patent Literature 2). The radiochemical yield means a yield of a target radioactive compound and is calculated by dividing the radioactivity of the target compound by the radioactivity of a raw material. However, even when DOTA, the concentration of which is set to be higher than $10^{-4}$ mol/L, is reacted with radioactive zirconium according to the disclosure of Non Patent Literature 2, almost the entire radioactive zirconium precipitates or adheres to a reaction vessel and cannot be collected, making the radiochemical yield a low yield of less than 10% in some cases.

Furthermore, for a drug for use in positron emission tomography (PET) (hereinafter, a PET drug), microdosing, in which a dose is an extremely minute amount of the order of microgram (μg), is often performed. Thus, it is considered that even a drug containing DOTA with a low concentration of about $10^{-5}$ mol/L, which is less than $10^{-4}$ mol/L, in its structure has a high possibility of labeling radioactive zirconium. In this case, DOTA and radioactive zirconium are desirably bonded to each other with a reaction rate higher than 90%. However, there is a problem in that even when DOTA with a low concentration of about $10^{-5}$ mol/L and radioactive zirconium are reacted based on reaction conditions by conventional technologies, the radiochemical yield is substantially 0%. This problem is a problem occurring in the same way in NOTA or the like with a low concentration.

The present invention has been made in view of the above, and an object thereof is to provide a method for synthesizing a zirconium complex, in which a zirconium complex can be synthesized by reacting a chelating agent such as DOTA or NOTA, even with a low concentration, and radioactive zirconium with a high reaction rate.

Solution to Problem

To solve the problem and achieve the object, a method for synthesizing a zirconium complex according to the present invention includes: mixing a solvent containing an organic substance having a dipole moment of 3.0 D or more, a chelating agent solution in which a chelating agent containing a structure represented by General Formula (1) or General Formula (2) is dissolved, and zirconium dissolved in an acidic solution, to obtain a mixed solution; and setting the mixed solution at a predetermined temperature or more to synthesize a zirconium complex,

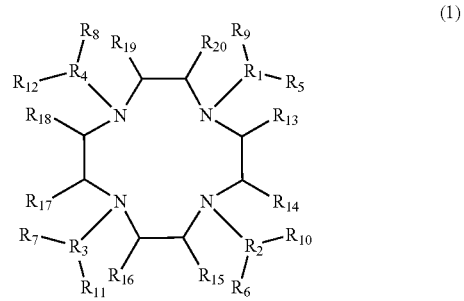

(1)

(2)

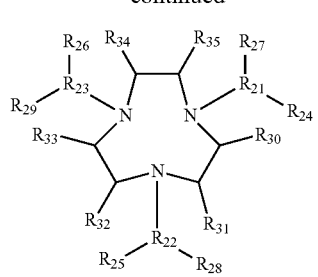

wherein in General Formula (1): $R_1$, $R_2$, $R_3$, and $R_4$ being each a hydrogen (—H) (in this case, none of $R_5$ to $R_{12}$ is further connected), a —CH— group, —$(CH_2)_n$CH— group, a —N(=O) $(CH_2)_n$NCH— group, or a —$(CH_2)_n$NC(=O) N— group; n being an integer of 0 or more; at least two of $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ being at least two selected from a carboxylic acid, a primary amide, hydroxamic acid, phosphonic acid, phosphoric acid, sulfonic acid, an alcohol, an amine, phenol, aniline, and an ester, a secondary amide, hydroxamic acid, and a phosphate that are each obtained by adding a substituent to the aforementioned, with the residual substituents being each a hydrogen, an alkyl chain, a tert-butyl blocked carboxylic acid, nitrobenzene, or a substituent-added alkyl chain; a positron emission tomography (PET) probe or a functional group facilitating bonding of a PET probe being optionally added to a functional group contained in $R_5$ to $R_{20}$; the functional group facilitating bonding being a carboxylic acid, a succinimide carboxylate, a tetrafluorophenol carboxylate, an alcohol, an amine, a thiol, isothiocyanate, maleimide, phenol, aniline, benzoic acid, phenyl isothiocyanate, or an alkyne, an azide, dibenzocyclooctyne (DBCO), bicyclononyne (BCN), trans-cyclooctene (TCO), norbornene, tetrazine, or methyltetrazine, which are each a click chemistry reagent; and $R_1$ to $R_{20}$ optionally having a structure of the functional group facilitating bonding or a condensed structure of a PET probe and the functional group facilitating bonding, and wherein in General Formula (2): $R_{21}$, $R_{22}$, and $R_{23}$ being each a hydrogen (—H) (in this case, none of $R_{24}$ to $R_{29}$ is further connected), a —CH— group, —$(CH_2)_n$CH— group, a —N(=O) $(CH_2)_n$NCH— group, or a —$(CH_2)_n$NC(=O) N— group; n being an integer of 0 or more; at least two of $R_{24}$, $R_{23}$, $R_{26}$, $R_{27}$, $R_{28}$, $R_{29}$, $R_{30}$, $R_{31}$, $R_{32}$, $R_{33}$, $R_{34}$, and $R_{35}$ being at least two selected from a carboxylic acid, a primary amide, hydroxamic acid, phosphonic acid, phosphoric acid, sulfonic acid, an alcohol, an amine, phenol, aniline, and an ester, a secondary amide, hydroxamic acid, and a phosphate that are each obtained by adding a substituent to the aforementioned, with the residual substituents being each a hydrogen, an alkyl chain, a tert-butyl blocked carboxylic acid, nitrobenzene, or a substituent-added alkyl chain; a PET probe or a functional group facilitating bonding of a PET probe being optionally added to a functional group contained in $R_{24}$ to $R_{35}$; the functional group facilitating bonding being the following functional group, a carboxylic acid, a succinimide carboxylate, a tetrafluorophenol carboxylate, an alcohol, an amine, a thiol, isothiocyanate, maleimide, phenol, aniline, benzoic acid, phenyl isothiocyanate, or an alkyne, an azide, DBCO, BCN, TCO, norbornene, tetrazine, or methyltetrazine, which are each a click chemistry reagent; and $R_{24}$ to $R_{35}$ optionally having a structure of the functional group facilitating bonding or a condensed structure of a PET probe and the functional group facilitating bonding.

Moreover, in the method for synthesizing a zirconium complex according to the present invention, the organic substance is at least one substance selected from the group consisting of dimethylsulfoxide (DMSO), N,N-dimethylformamide (DMF), N-methylformamide (NMF), N-methylpyrrolidone (NMP), and urea.

Moreover, in the method for synthesizing a zirconium complex according to the present invention, a concentration of the organic substance is 1 vol % or more and 95 vol % or less.

Moreover, in the method for synthesizing a zirconium complex according to the present invention, the predetermined temperature is 35° C. or more.

Moreover, in the method for synthesizing a zirconium complex according to the present invention, the solvent is a solvent purified with a metal removing agent.

Moreover, in the method for synthesizing a zirconium complex according to the present invention, the acidic solution is hydrochloric acid.

Moreover, in the method for synthesizing a zirconium complex according to the present invention, zirconium dissolved in the acidic solution is mixed into a solution in which the solvent and the chelating agent solution are mixed together immediately before heating at the predetermined temperature or more or after the heating.

Moreover, in the method for synthesizing a zirconium complex according to the present invention, at least one of $R_5$ to $R_{20}$ in General Formula (1) or at least one of $R_{24}$ to $R_{35}$ in General Formula (2) bonds a molecular probe or bonds a linker to a molecular probe, via at least one structure selected from the group consisting of Chemical Formulae (16) to (21) and (26).

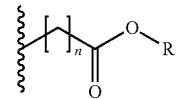

(16)

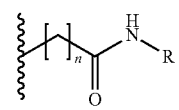

(17)

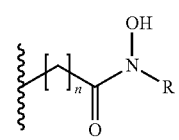

(18)

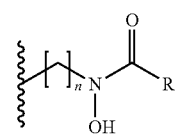

(19)

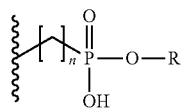

(20)

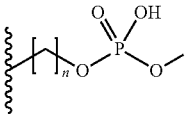

(21)

-continued

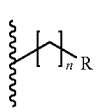
(26)

Moreover, in the method for synthesizing a zirconium complex according to the present invention, the molecular probe is a protein, a peptide, or a low-molecular weight organic compound. Moreover, in the method for synthesizing a zirconium complex according to the present invention, the protein or the peptide includes a natural amino acid, a non-natural amino acid, or both the natural amino acid and the non-natural amino acid and has a linear-chain structure or a cyclic structure. Moreover, in the method for synthesizing a zirconium complex according to the present invention, the linker is polyethylene glycol, an alkyl chain, piperazine, or a complex thereof.

Moreover, in the method for synthesizing a zirconium complex according the present invention, oxalic acid is added to the acidic solution to adjust a concentration of the oxalic acid to be $10^{-6}$ mol/L or more and less than $10^{-4}$ mol/L.

Advantageous Effects of Invention

The method for synthesizing a zirconium complex according to the present invention can synthesize a zirconium complex by reacting DOTA, even with a low concentration, and radioactive zirconium with a high radiochemical yield.

DESCRIPTION OF EMBODIMENTS

Figure 1:
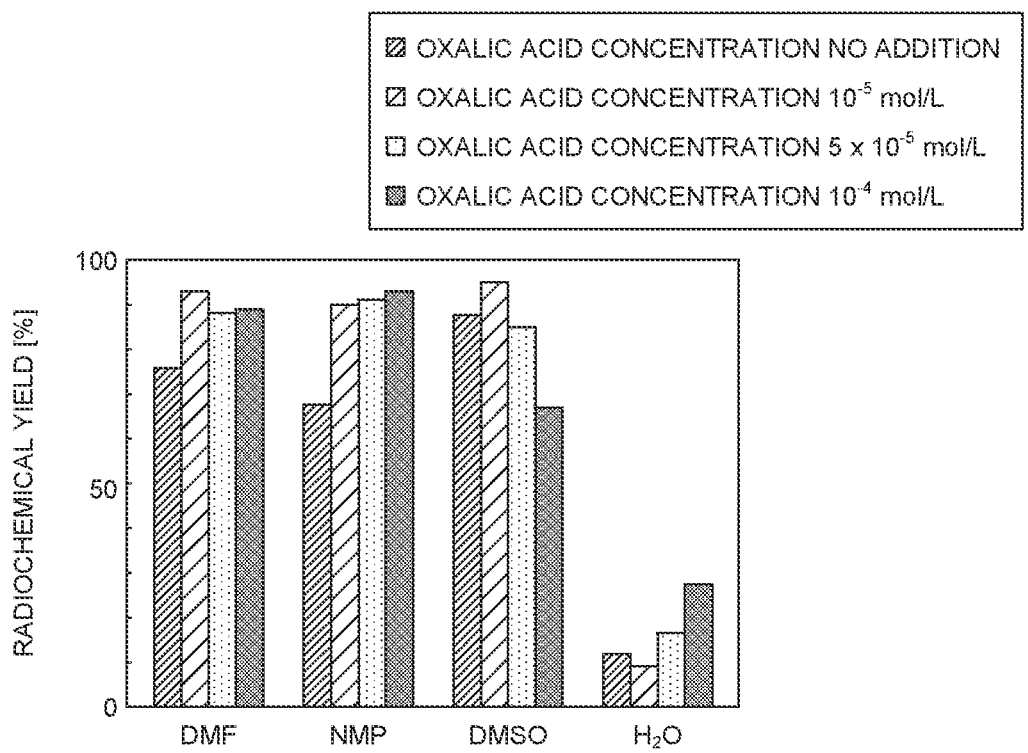
FIG. 1 is a graph illustrating an influence of oxalic acid on the radiochemical yield of DOTA-$^{89}$Zr in accordance with an oxalic acid concentration.

The following describes one embodiment of the present invention with reference to the accompanying drawings. The one embodiment described below does not limit the present invention. First, in describing the one embodiment of the present invention, to facilitate understanding of the present invention, the following describes experiments and earnest studies performed to solve the problem by the inventor of the present invention.

The following first describes a problem with conventional technologies about a reaction of radioactive zirconium (hereinafter, also referred to as zirconium, Zr, or $^{89}$Zr) as an object of the earnest studies by the inventor of the present invention and DOTA as a compound represented by General Formula (1) below.

DOTA indicated by General Formula (1) below can easily bond to radio isotopes (RIs) of many kinds of metals and has thus conventionally widely been used as a general-purpose chelating agent. Furthermore, in many drugs, methods for synthesizing DOTA derivatives have been established, and DOTA and derivatives thereof (1,4,7,10-tetrakis(carbamoyl-methyl)-1,4,7,10-tetraazacyclododecane (DOTAM) and 1,4,7,10-tetraazacyclododecane-1,4,7,10-tetra(methylene phosphonic acid) (DOTP), for example) are easily available.

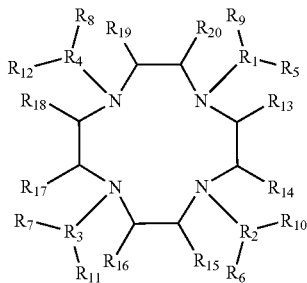
(1)

In General Formula (1), $R_1$, $R_2$, $R_3$, and $R_4$ are each a hydrogen (—H) (in this case, none of $R_5$ to $R_{12}$ is further connected), a —CH— group, —(CH$_2$)$_n$CH— group, a —N(=O) (CH$_2$)$_n$NCH— group, or a —(CH$_2$)$_n$NC(=O) N— group. n is an integer of 0 or more. At least two of $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ are at least two selected from a carboxylic acid, a primary amide, hydroxamic acid, phosphonic acid, phosphoric acid, sulfonic acid, an alcohol, an amine, phenol, aniline, and an ester, a secondary amide, hydroxamic acid, and a phosphate that are each obtained by adding a substituent to the aforementioned, with the residual substituents being each a hydrogen, an alkyl chain, a tert-butyl blocked carboxylic acid, nitrobenzene, or a substituent-added alkyl chain. A PET probe or a functional group facilitating bonding of a PET probe is optionally added to a functional group contained in $R_5$ to $R_{20}$. The functional group facilitating bonding is a carboxylic acid, a succinimide carboxylate, a tetrafluorophenol carboxylate, an alcohol, an amine, a thiol, isothiocyanate, maleimide, phenol, aniline, benzoic acid, phenyl isothiocyanate, or an alkyne, an azide, dibenzocyclooctyne (DBCO), bicyclononyne (BCN), trans-cyclooctene (TCO), norbornene, tetrazine, or methyltetrazine, which are each a click chemistry reagent. $R_5$ to $R_{20}$ optionally have a structure of the functional group facilitating bonding or a condensed structure of a PET probe and the functional group facilitating bonding.

The functional group described above may have still another compound bonded via an ester bond, an amide bond, or the like or have branching for holding another compound from an alkyl chain. Specific examples include crosslink-forming functional groups such as succinimide, isothiocyanate, an amine, a thiol, and a carboxylic acid and click chemistry-oriented functional groups such as an azide, an alkene, an alkyne, and tetrazine. Furthermore, a drug for use in molecular imaging may be bonded via these crosslink-forming functional groups.

For each of $R_1$ to $R_4$, the structure represented by General Formula (3) below may be employed; specifically, one selected from the structures represented by Chemical Formulae (3-1) to (3-4) can be employed; n in Chemical Formulae (3-2) to (3-4) is an integer of 0 or more.

(3)
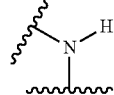

(3-1)
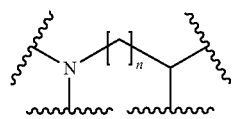

(3-2)
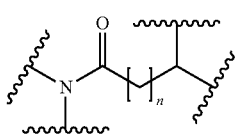

(3-3)
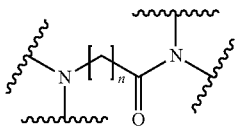

(3-4)
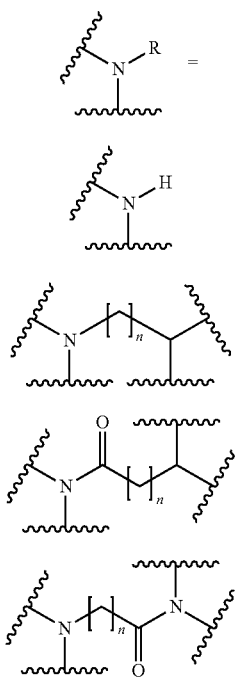

For each of $R_5$ to $R_{20}$, one selected from the structures represented by General Formulae (4) to (21) below can be employed; n in General Formulae (4) to (21) is an integer of 0 or more. General Formulae (4) to (21) are functional groups that are likely to coordinately bond to metal. At least two of $R_5$ to $R_{12}$ are preferably selected from the structures represented by General Formulae (4) to (21). For each of $R_5$ to $R_{20}$, one selected from the structures represented by General Formulae (22) to (26) below can be employed. The structures represented by General Formulae (22) to (26) are structures that do not form any complex with a metal ion or are hard to form a complex therewith. Any of $R_5$ to $R_{20}$ in General Formula (1) may bond a molecular probe or bond a linker to a molecular probe via at least one structure selected from the group consisting of Chemical Formulae (16) to (21) and (26).

(4)
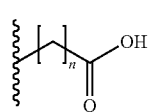

(5)
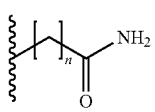

(6)
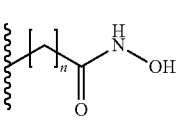

(7)
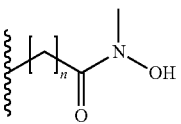

(8)
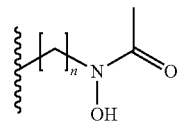

(9)
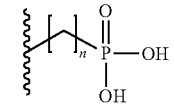

(10)
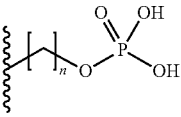

(11)
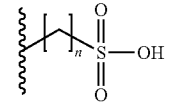

(12)
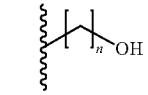

(13)
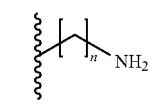

(14)
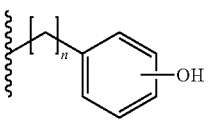

(15)
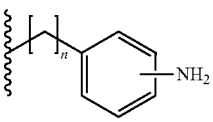

(16)
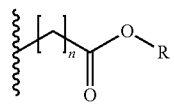

(17)
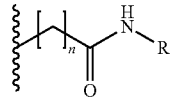

(18)
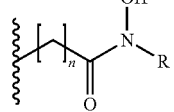

(19)
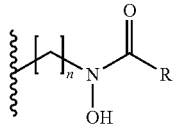

(20)
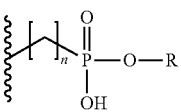

(21) 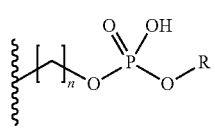

(22) 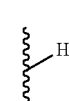

(23) 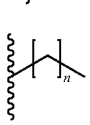

(24) 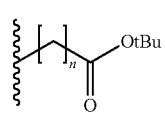

(25) 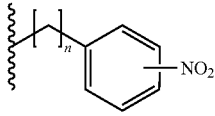

(26) 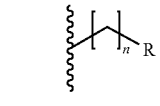

A complex of DOTA or a derivative of DOTA and a drug such as an antibody, a protein, a peptide, or a low-molecular weight organic compound as an object of a molecular imaging experiment can also be used. For the protein or the peptide, one including a natural amino acid, a non-natural amino acid, or both the natural amino acid and the non-natural amino acid and having a linear-chain structure or a cyclic structure can be employed. Specifically, a method amidating one carboxylic acid in the structure of DOTA and crosslinking it with the drug and a substance obtained through crosslinking from a cyclic alkyl chain in the structure of DOTA are known. Bonding may be performed by interposing an appropriate linker such as polyethylene glycol between DOTA and the drug; specifically, it is also used for high-molecular weight pharmaceuticals such as antibodies or low-molecular weight pharmaceuticals such as PSMA-617. The linker is typically, but is not necessarily limited to, polyethylene glycol, an alkyl chain, piperazine, or a complex of polyethylene glycol, an alkyl chain, or piperazine. In the present invention, the substance as an object of bonding is not limited to DOTA and also includes derivatives thereof and complexes with drugs. That is, for R in each of General Formulae (16) to (21) and (26) described above, one selected from the structures represented by Chemical Formulae (27) to (47) below can be employed. $^{89}$Zr may be complexed in the DOTA structure after bonding the drug to R, or the drug may be bonded to R after complexing $^{89}$Zr.

(27) 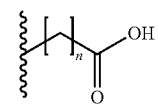

(28) 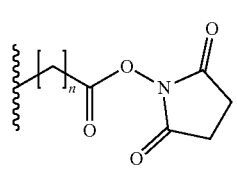

(29) 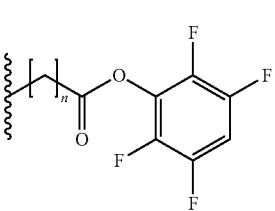

(30) 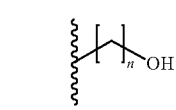

(31) 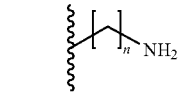

(32) 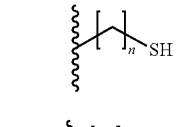

(33) 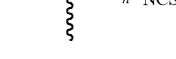

(34) 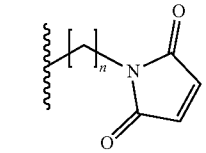

(35) 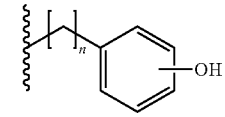

(36) 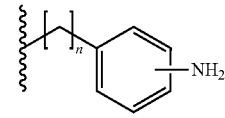

(37) 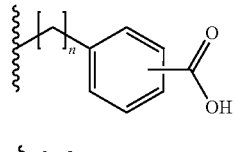

(38) 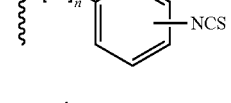

(39) 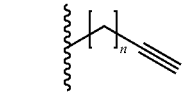

-continued

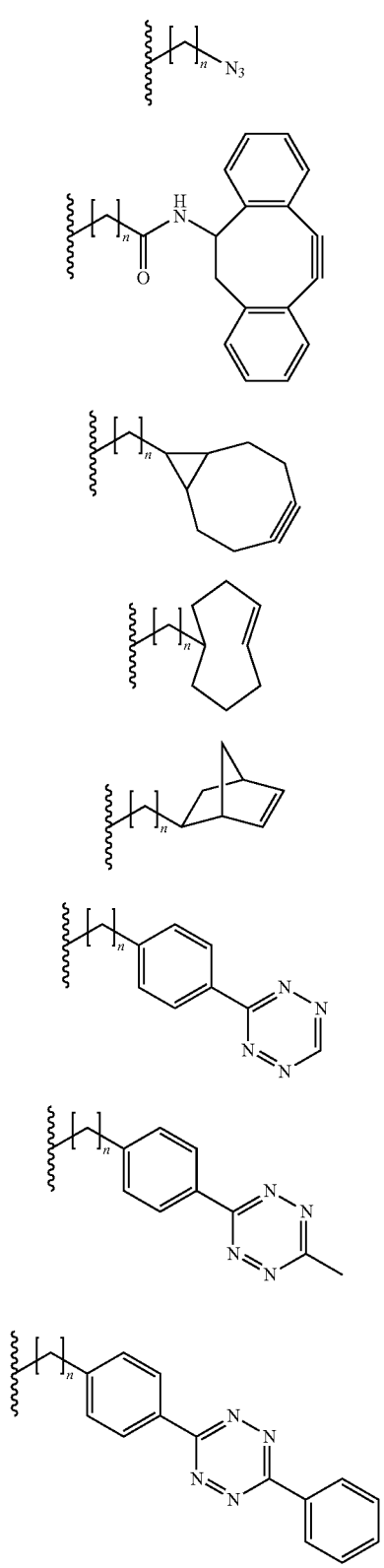

(40)
(41)
(42)
(43)
(44)
(45)
(46)
(47)

As described above, $^{89}$Zr has an appropriate half-life and high resolution and is thus a nuclide extremely suitable for use in medical imaging. As the chelating agent for use in labeling of $^{89}$Zr, deferoxamine (DFO) indicated by Chemical Formula (100) below has conventionally been used, for example. DFO, having weak bonding force with metal radioactive nuclides other than Zr, is substantially an exclusive chelating agent for radioactive z-irconium and thus has a problem in that it has poor versatility and cannot be used also for imaging of other nuclides. Thus, a complex of DFO and the PET probe is required to be synthesized only for $^{89}$Zr imaging, causing a problem of an increased cost of synthesis. In addition, DFO has insufficient bonding force in bonding to Zr, causing a problem in that radioactive zirconium separates from a drug in living bodies in molecular imaging.

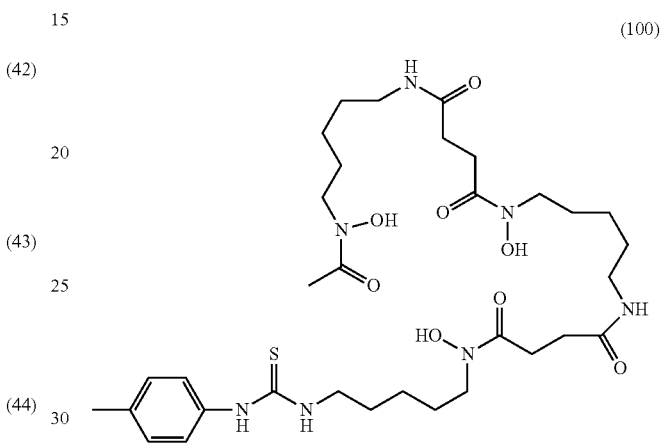

(100)

Given these circumstances, various methods using DOTA as the chelating agent described above and $^{89}$Zr are being studied. When $^{89}$Zr and DOTA are bonded together, the bonding itself is strong, thus giving an advantage that when medical imaging such as PET is performed, $^{89}$Zr is hard to separate from the chelating agent in human bodies, and thus image quality can be improved. Furthermore, existing drugs containing DOTA developed for other nuclides such as $^{68}$Ga can be diverted to chelating agents for $^{89}$Zr, thus achieving a low cost in development of drugs labeling $^{89}$Zr.

However, there is a problem in that bonding between DOTA described above and $^{89}$Zr is extremely difficult. Specifically, as described in Non Patent Literature 2, to bond $^{89}$Zr and DOTA together in line with the conventional method bonding $^{89}$Zr and the chelating agent together, it was necessary that $^{89}$Zr and DOTA be added to a HEPES buffer solution, the reaction temperature be 90° C. or more or preferably 95° C. or more, the reaction time be 1 hour, and the concentration of DOTA be $10^{-4}$ mol/L or more. The inventor of the present invention examined a radiochemical yield when $^{89}$Zr and DOTA were reacted in accordance with the conditions described above, and it was revealed that even when an experiment was performed in accordance with the method described in Non Patent Literature 2, the reproducibility of results was low and the radiochemical yield was low in some cases. When $^{89}$Zr is used for medical imaging, it is desirable that even DOTA with a concentration of about $10^{-5}$ mol/L be able to bond to $^{89}$Zr. However, when the inventor of the present invention examined the radiochemical yield on this condition, there was a problem in that the radiochemical yield was substantially 0%. The inventor of the present invention performed an experiment, and it was confirmed that the radiochemical yield being substantially 0% was caused by adhesion of the bulk of $^{89}$Zr to a reaction vessel such as a microtube. The inventor of the present invention studied this point and assumed that $^{89}$Zr precipitated as zirconium hydroxide to adhere to the reaction vessel.

The inventor of the present invention variously studied the problem and the cause about the foregoing reaction of $^{89}$Zr and DOTA and has thought that to obtain a high radiochemical yield in a complex forming reaction of $^{89}$Zr and DOTA, it is necessary that a reaction rate be increased or that formation of the hydroxide of $^{89}$Zr be prevented. The inventor of the present invention performed various experiments and earnest studies on the increase in the reaction rate and prevention of the formation of the hydroxide. That is, the inventor of the present invention performed experiments in which metal ions such as iron ions ($Fe^{3+}$), titanium ions ($Ti^{4+}$), and yttrium ions ($Y^{3+}$) as impurities other than $^{89}$Zr were mixed so as to have a molar concentration equal to DOTA with a concentration of $10^{-2}$ mol/L to be reacted. As listed in Table 1, it was revealed that the bonding rate, that is, the radiochemical yield of $^{89}$Zr reduced to about 10% to 32%. That is, it is revealed that DOTA reacts with the other metal ions in preference to Zr and that the other metal ions and Zr are not exchanged after the reaction. Thus, the metal ions as impurities are preferably removed in the present reaction. Specifically, metals as impurities are preferably removed by a metal removing agent such as a styrene-vinylbenzene copolymer containing iminodiacetate ions in the buffer solution and the organic solvent for use in the reaction of $^{89}$Zr and DOTA. The purity of a purified solution of $^{89}$Zr may be improved by employing the method described in Patent Literature 1.

TABLE 1

| Added metal ion | Bonding rate of $^{89}$Zr |
|---|---|
| No addition | 92% |
| $Y^{3+}$ | 10% |
| $Ti^{4+}$ | 12% |
| $Fe^{3+}$ | 32% |

The inventor of the present invention added dimethylsulfoxide (DMSO) indicated by Chemical Formula (200) below to an aqueous buffer solution to react $^{89}$Zr and DOTA, and it was confirmed that the reaction time was about 30 minutes, which was a half of conventional 1 hour, and that the radiochemical yield improved up to 95%. Furthermore, a phenomenon in which $^{89}$Zr becomes zirconium hydroxide to adhere to the reaction vessel was almost unobserved.

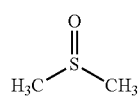

(200)

According to studies by the inventor of the present invention, in a mixed solution of DOTA and $^{89}$Zr, first, a reaction intermediate complex indicated on the left side of Reaction Formulae (301a) and (301b) below is formed. Subsequently, it is considered that this reaction intermediate complex is heated to change to DOTA-$^{89}$Zr indicated on the right side of Reaction Formula (301a). Zr ions also strongly bond to water molecules and hydroxide ions, and thus it is also assumed that $^{89}$Zr is divided from the reaction intermediate complex together with hydrating water by the heating to change to zirconium hydroxide indicated on the right side of Reaction Formula (301b). It is considered that the low yield based on the conventional reaction conditions is caused by the fact that zirconium hydroxide reacted as in Reaction Formula (301b) adheres to the reaction vessel or the like to become inactive in reactivity.

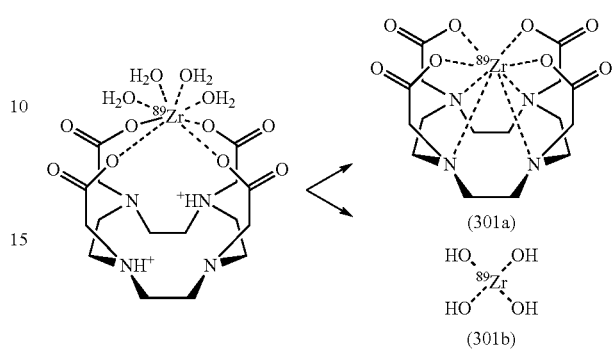

On the other hand, it is expected that when a highly polar substance such as DMSO is added, the added substance coordinates to $^{89}$Zr in preference to water in the reaction intermediate complex. It is considered that as indicated in Reaction Formula (302) below, unlike the case in which water coordinates thereto, the thus generated reaction intermediate complex cannot cause a reaction to produce zirconium hydroxide, and thus the bulk of $^{89}$Zr is generated as DOTA-$^{89}$Zr.

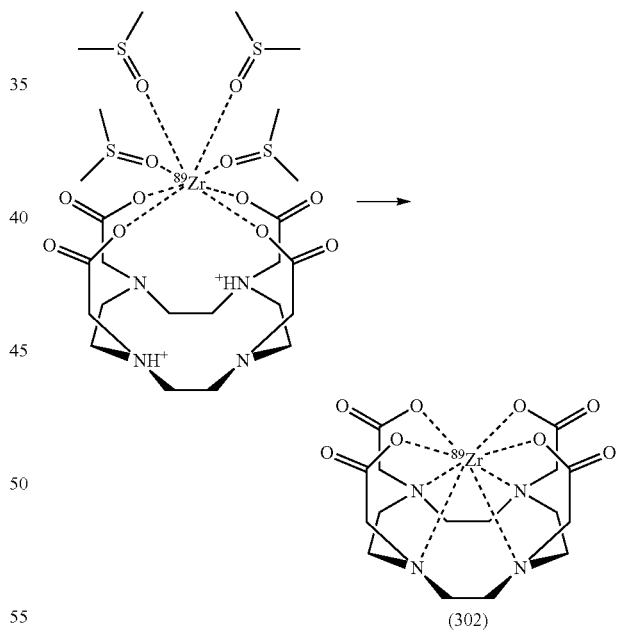

The inventor of the present invention performed various experiments to find out that the radiochemical yield of DOTA-$^{89}$Zr changes by a method for purifying $^{89}$Zr. Specifically, when a $^{89}$Zr solution prepared by the method of purification described in Non Patent Literature 1 and Non Patent Literature 2 was used, the yield was extremely low. On the other hand, it was revealed that when a $^{89}$Zr solution purified by the method described in Patent Literature 2 was used, the yield was high. The inventor of the present invention has earnestly studied the difference in the yield to find out that it is caused by an oxalic acid concentration contained in the purified $^{89}$Zr solution. $^{89}$Zr is first roughly purified as an oxalic acidic solution using a hydroxamic acid resin and is then replaced by a hydrochloric acidic solution using an anion exchange resin. In the method described in Non Patent Literature 1 and Non Patent Literature 2, the anion exchange resin to which 39Zr adsorbs is washed with purified water, and then $^{89}$Zr is eluted with hydrochloric acid with a concentration of 1 mol/L. However, according to analysis performed by the inventor of the present invention, oxalic acid of the order of $10^{-3}$ mol/L is dissolved in the $^{89}$Zr solution eluted by the method described in Non Patent Literature 1 and Non Patent Literature 2. On the other hand, in the method described in Patent Literature 2, the anion exchange resin is washed with diluted hydrochloric acid before eluting $^{89}$Zr, whereby the oxalic acid concentration can be reduced; specifically, it was confirmed that the dissolved oxalic acid concentration was able to be reduced to the order of $10^{-6}$ mol/L.

Figure 2:
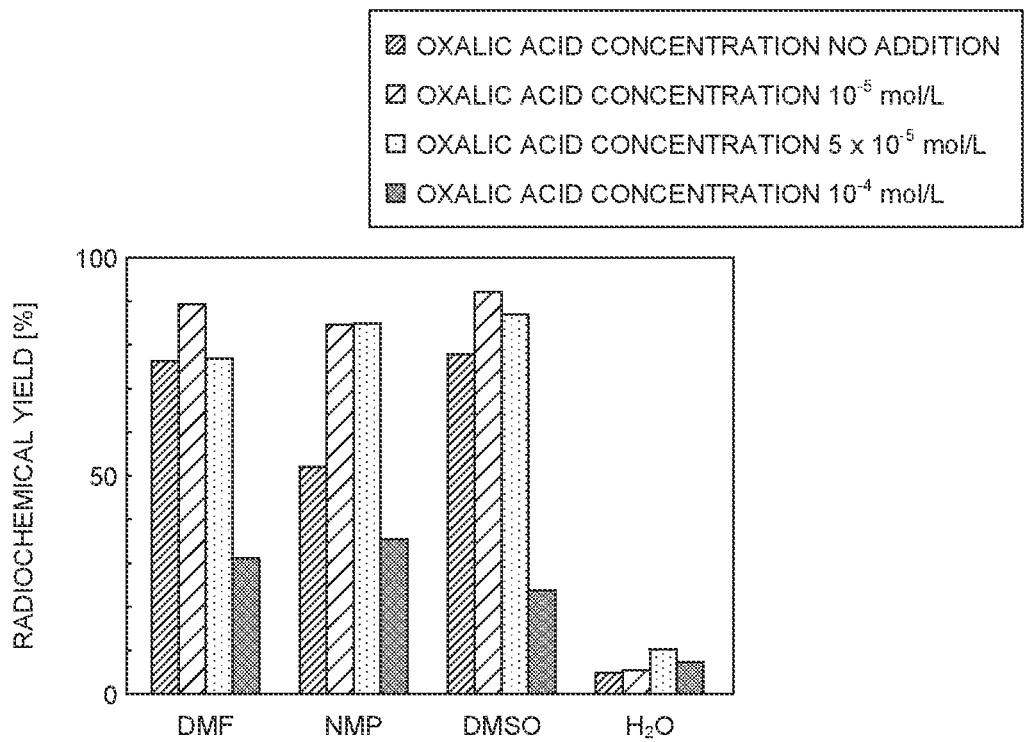
FIG. 2 is a graph illustrating an influence of oxalic acid on the radiochemical yield of a $^{89}$Zr-DOTA-containing PET probe in accordance with the oxalic acid concentration.

Subsequently, the inventor of the present invention studied an influence of the oxalic acid concentration on the radiochemical yield. As the drug, DOTA and a DOTA-containing PET probe (product name: PSMA-617, for example) were used. The purified $^{89}$Zr solution was prepared using the method described in Patent Literature 2, and oxalic acid was further added thereto to adjust the oxalic acid concentration. FIG. 1 and FIG. 2 illustrate results when an organic solvent and the $^{89}$Zr solution were added to an aqueous buffer solution to be reacted. FIG. 1 is a graph illustrating an influence of oxalic acid on the radiochemical yield of DOTA-$^{89}$Zr in accordance with the oxalic acid concentration, whereas FIG. 2 is a graph illustrating an influence of oxalic acid on the radiochemical yield of a $^{89}$Zr-DOTA-containing PET probe in accordance with the oxalic acid concentration.

From FIG. 1 and FIG. 2, the inventor of the present invention has found that there is a preferable oxalic acid concentration in terms of the oxalic acid concentration. That is, the inventor of the present invention has found that the oxalic acid concentration is preferably $10^{-6}$ mol/L or more, typically $10^{-5}$ mol/L or more and less than $10^{-4}$ mol/L, and suitably $10^{-5}$ mol/L or more and $5\times10^{-5}$ mol/L or less, although it depends on the drug or the solvent. According to studies by the inventor of the present invention, $^{89}$Zr is likely to adhere to a vessel in a condition in which oxalic acid is not added, and thus it is assumed that when the oxalic acid concentration is low, zirconium hydroxide is likely to be purified. On the other hand, the inventor of the present invention has also found that when the oxalic acid concentration is high, although adhesion of $^{89}$Zr to the vessel hardly occurs, a reaction rate reduces. It is considered that this is because although oxalic acid and $^{89}$Zr form a complex to prevent generation of the hydroxide, complex formation with the drug such as DOTA is inhibited. Consequently, an oxalic acid concentration that does not inhibit the reaction with DOTA while preventing generation of the hydroxide is preferred; it is considered that the range of this oxalic acid concentration is $10^{-6}$ mol/L or more, typically $10^{-5}$ mol/L or more and less than $10^{-4}$ mol/L, and suitably $10^{-5}$ mol/L or more and $5\times10^{-5}$ mol/L or less described above.

According to the knowledge of the inventor of the present invention, the foregoing result can be obtained similarly for zirconium-bonding organic substances such as citric acid and ascorbic acid. The appropriate concentration range may vary from substance to substance. In the experiment of organic solvent concentration dependence described above, it is assumed that the oxalic acid concentration was in a range of about $10^{-6}$ mol/L to $10^{-5}$ mol/L.

As the aqueous buffer solution, a buffer solution having buffering ability in a neutral range and has small interaction with metal ions is preferred. Specific examples of the aqueous buffer solution include, but are not necessarily limited to, Good's buffers and Tris buffer solutions.

The inventor of the present invention performed further earnest studies to find that, in addition to the knowledge obtained as described above, a time elapsed from purification of radioactive zirconium is also important. That is, the inventor of the present invention has found that radioactive zirconium elapsed for a predetermined time as the oxalic acidic solution, even when it is replaced by the hydrochloric acidic solution by removing oxalic acid with the ion exchange resin, reduces in the radiochemical yield. Specifically, when radioactive zirconium purified as the oxalic acidic solution was additionally purified with the anion exchange resin within 1 hour to be reacted with DOTA, the radiochemical yield was about 95%. On the other hand, when radioactive zirconium purified as the oxalic acidic solution was additionally purified after a lapse of 24 hours, the radiochemical yield was 83%, whereas when it was additionally purified after a lapse of 120 hours, the radiochemical yield was 49%. According to earnest studies by the inventor of the present invention, it is considered that there is a possibility that an extremely small amount of oxalic acid precipitates as fine particles, and that an oxalic acid concentration mixing into a $^{89}$Zr purified solution changes. Thus, in two-step radioactive zirconium purification, the first step and the second step are desirably performed within 24 hours and are more desirably performed within 1 hour.

As an alternative to DOTA, a tricyclic such as NOTA indicated by General Formula (2) below or the like may be used.

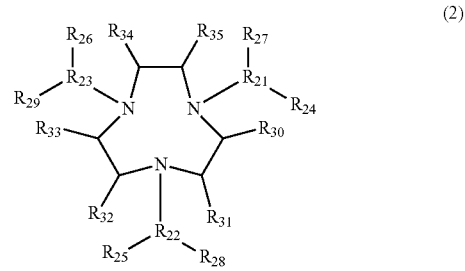

(2)

In General Formula (2), $R_{21}$, $R_{22}$, and $R_{23}$ are each a hydrogen (—H) (in this case, none of $R_{24}$ to $R_{29}$ is further connected), a —CH— group, —(CH$_2$)$_n$CH— group, a —N(=O) (CH$_2$)$_n$NCH— group, or a —(CH$_2$)$_n$NC(=O) N— group. n is an integer of 0 or more. At least two of $R_{24}$, $R_{25}$, $R_{26}$, $R_{27}$, $R_{28}$, $R_{29}$, $R_{30}$, $R_{31}$, $R_{32}$, $R_{33}$, $R_{34}$, and $R_{35}$ are at least two selected from a carboxylic acid, a primary amide, hydroxamic acid, phosphonic acid, phosphoric acid, sulfonic acid, an alcohol, an amine, phenol, aniline, and an ester, a secondary amide, hydroxamic acid, and a phosphate that are each obtained by adding a substituent to the aforementioned, with the residual substituents being each a hydrogen, an alkyl chain, a tert-butyl blocked carboxylic acid, nitrobenzene, or a substituent-added alkyl chain. A PET probe or a functional group facilitating bonding of a PET probe is optionally added to a functional group contained in $R_{24}$ to $R_{35}$. The functional group facilitating bonding is the following functional group: a carboxylic acid, a succinimide carboxylate, a tetrafluorophenol carboxylate, an alcohol, an amine, a thiol, isothiocyanate, maleimide, phenol, aniline, benzoic acid, phenyl isothioyanate, or an alkyne, an azide, DBCO, BCN, TCO, norbornene, tetrazine, or methyltetrazine, which are each a click chemistry reagent. $R_{24}$ to $R_{35}$ optionally have a structure of the functional group facilitating bonding or a condensed structure of a PET probe and the functional group facilitating bonding.

The functional group described above may have still another compound bonded via an ester bond, an amide bond, or the like or have branching for holding another compound from an alkyl chain. Specific examples include crosslink-forming functional groups such as succinimide, isothiocyanate, an amine, a thiol, and a carboxylic acid and click chemistry-oriented functional groups such as an azide, an alkene, an alkyne, and tetrazine. Furthermore, a drug for use in molecular imaging may be bonded via these crosslink-forming functional groups.

For each of $R_{21}$ to $R_{23}$, the structure represented by General Formula (3) below may be employed; specifically, one selected from the structures represented by Chemical Formulae (3-1) to (3-4) can be employed; n in Chemical Formulae (3-2) to (3-4) is an integer of 0 or more.

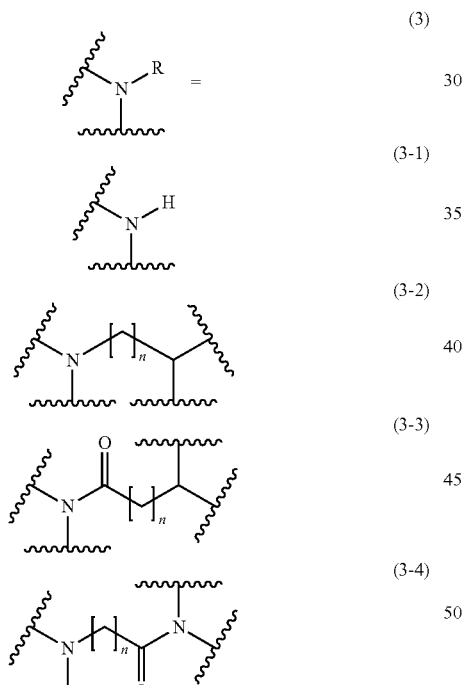

For each of $R_{24}$ to $R_{35}$, one selected from the structures represented by General Formulae (4) to (21) below can be employed; n in General Formulae (4) to (21) is an integer of 0 or more. For each of $R_{24}$ to $R_{35}$, one selected from the structures represented by General Formulae (22) to (26) below can be employed. The structures represented by General Formulae (22) to (26) are structures that do not form any complex with a metal ion or are hard to form a complex therewith. Any of $R_{24}$ to $R_{35}$ in General Formula (2) may bond a molecular probe or bond a linker to a molecular probe via at least one structure selected from the group consisting of Chemical Formulae (16) to (21) and (26).

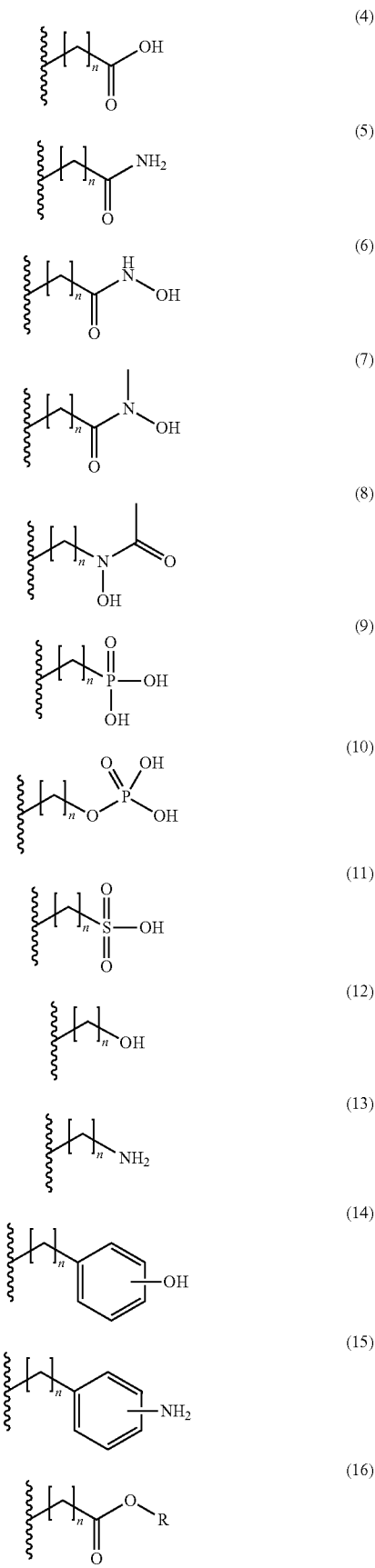

-continued

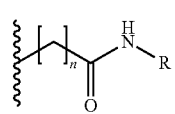  (17)

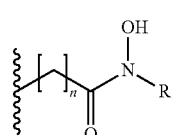  (18)

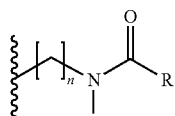  (19)

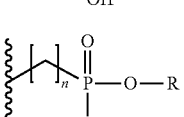  (20)

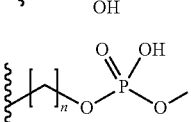  (21)

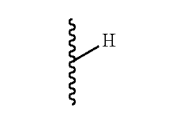  (22)

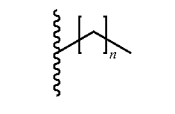  (23)

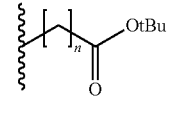  (24)

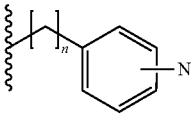  (25)

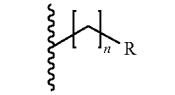  (26)

A complex of NOTA or a derivative of NOTA and a drug such as an antibody, a protein, a peptide, or a low-molecular weight organic compound as an object of a molecular imaging experiment can also be used. For the protein or the peptide, one including a natural amino acid, a non-natural amino acid, or both the natural amino acid and the non-natural amino acid and having a linear-chain structure or a cyclic structure can be employed. Specifically, a method amidating one carboxylic acid in the structure of NOTA and crosslinking it with the drug and a substance obtained through crosslinking from a cyclic alkyl chain in the structure of NOTA are known. Bonding may be performed by interposing an appropriate linker such as polyethylene glycol between NOTA and the drug; specifically, it is also used for high-molecular weight pharmaceuticals such as antibodies or low-molecular weight pharmaceuticals such as PSMA-617. The linker is typically, but is not necessarily limited to, polyethylene glycol, an alkyl chain, piperazine, or a complex of polyethylene glycol, an alkyl chain, or piperazine. In the present invention, the substance as an object of bonding is not limited to NOTA and also includes derivatives thereof and complexes with drugs. That is, for R in each of General Formulae (16) to (21) and (26) described above, one selected from the structures represented by Chemical Formulae (27) to (47) below can be employed. $^{89}$Zr may be complexed in the NOTA structure after bonding the drug to R, or the drug may be bonded to R after complexing $^{89}$Zr.

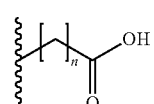  (27)

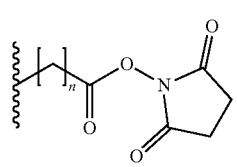  (28)

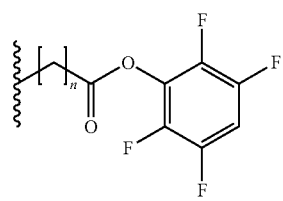  (29)

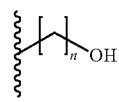  (30)

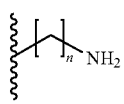  (31)

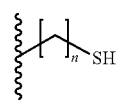  (32)

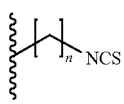  (33)

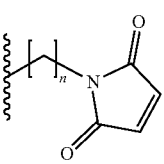  (34)

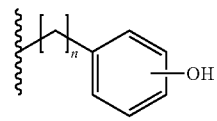  (35)

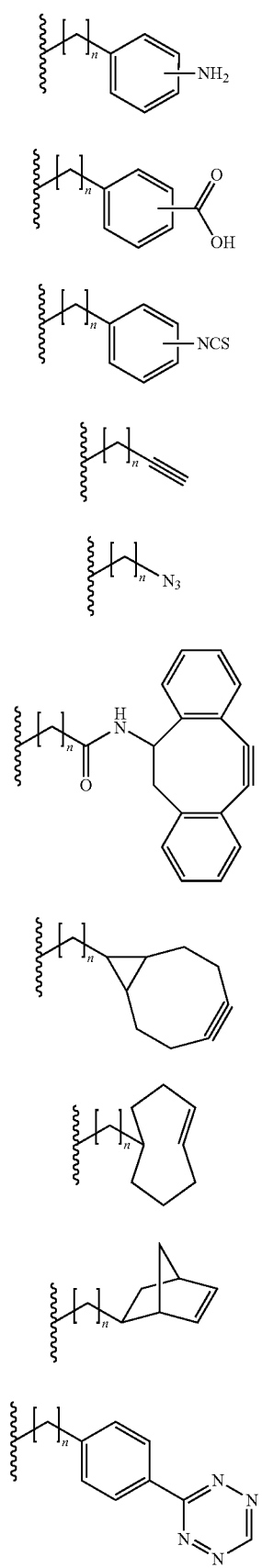
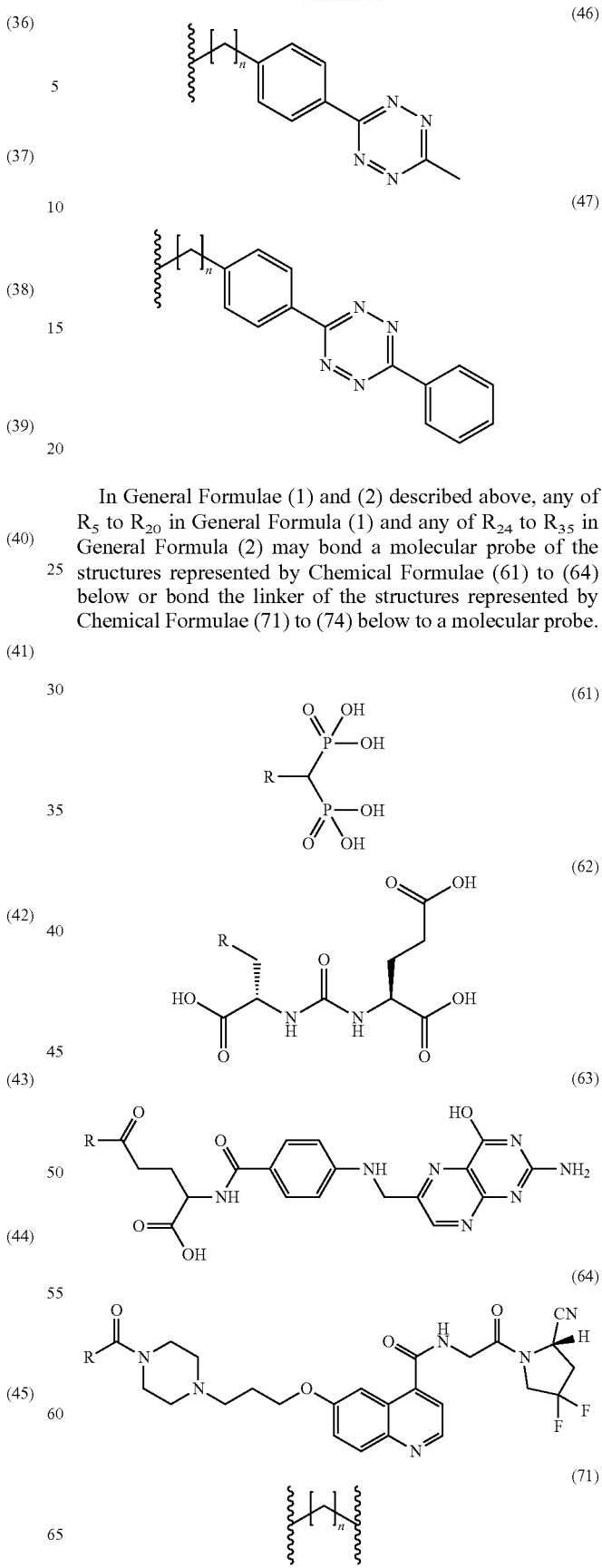
In General Formulae (1) and (2) described above, any of $R_5$ to $R_{20}$ in General Formula (1) and any of $R_{24}$ to $R_{35}$ in General Formula (2) may bond a molecular probe of the structures represented by Chemical Formulae (61) to (64) below or bond the linker of the structures represented by Chemical Formulae (71) to (74) below to a molecular probe.

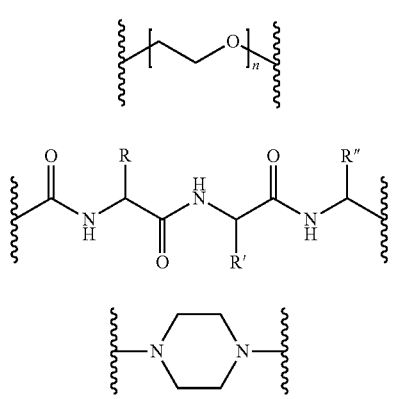

For DOTA represented by General Formula (1), the structures reacted as in Reaction Formulae (1-1) to (1-13) below can also be employed. In Reaction Formulae (1-1) to (1-13), represented in order from the left are a DOTA derivative, a substance desired to be bonded (written above the arrow), and a structure after condensation. Reaction Formulae (1-11) to (1-13) are click chemistry-oriented methods of bonding.

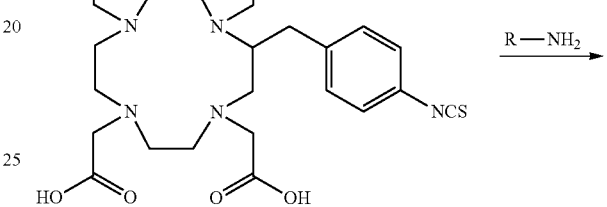

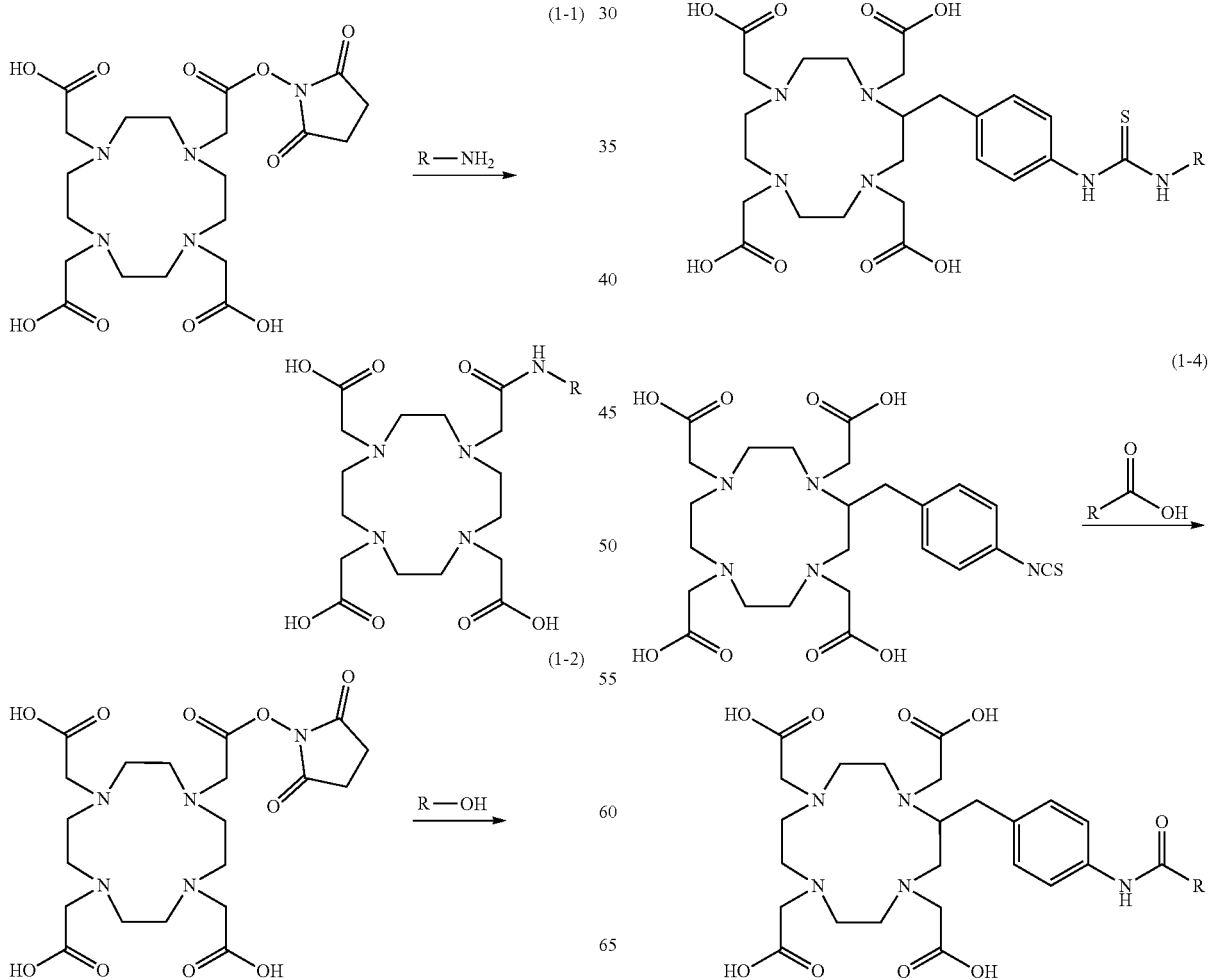

25
-continued
(1-5)
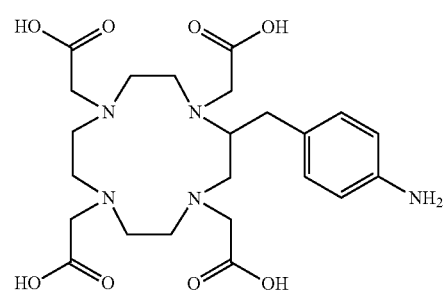 → R—NCS → 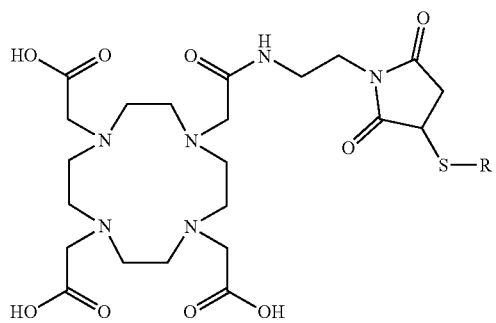
26
-continued
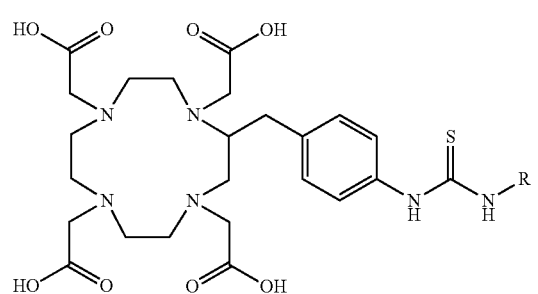
(1-6)
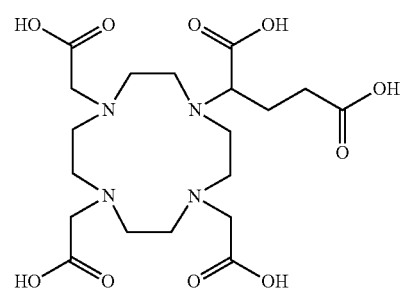 → R—NH₂ → 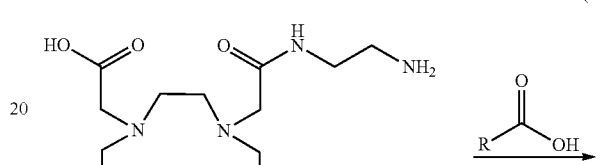
(1-8)
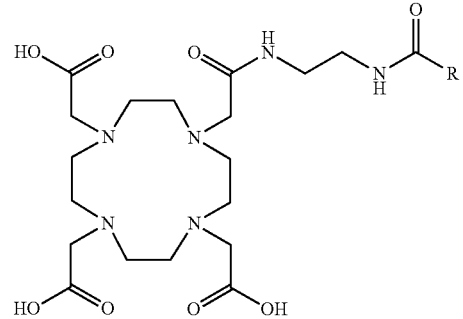 → 
(1-7)
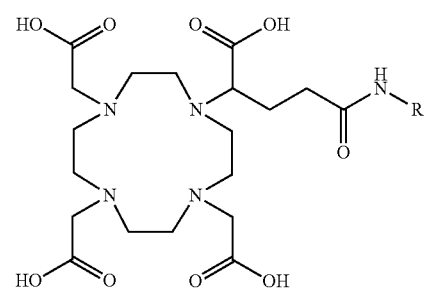 → R—SH →
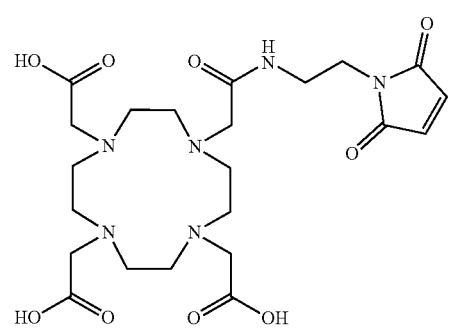 → R—NCS → 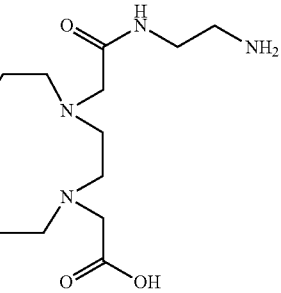
(1-9)
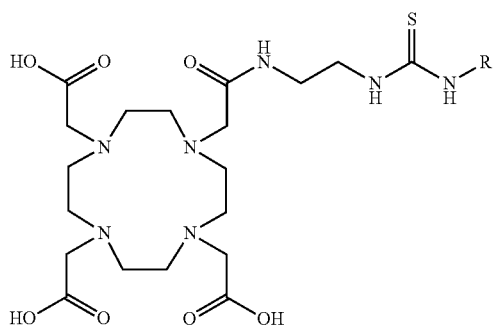

(1-10)
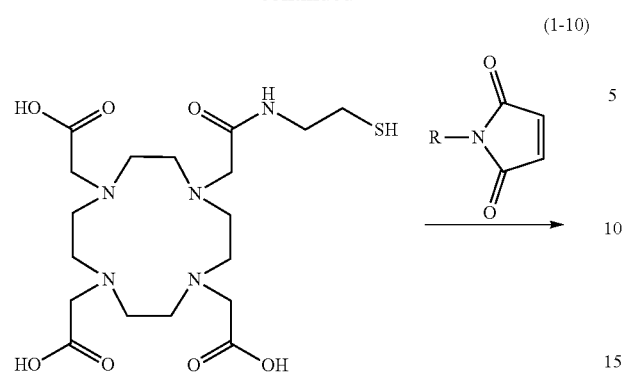
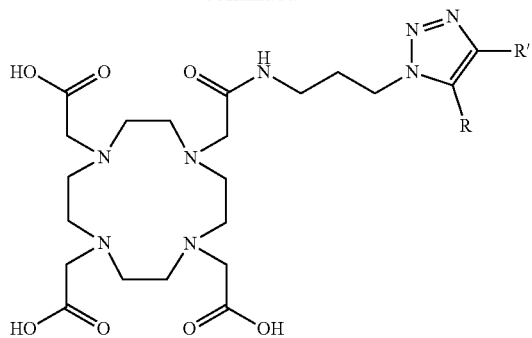
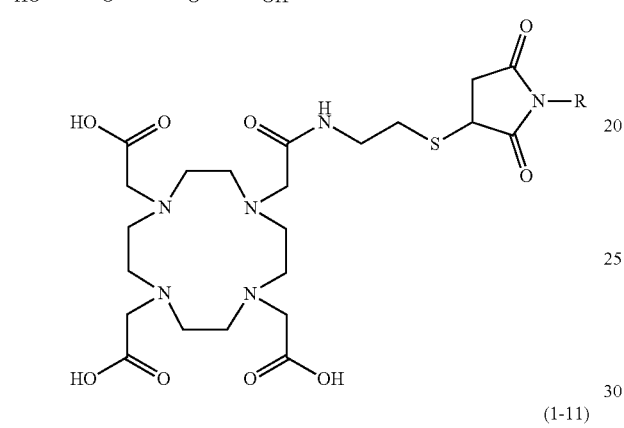
(1-11)
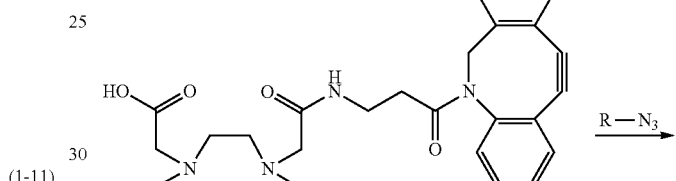
(1-13)
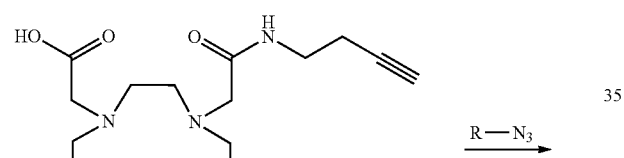
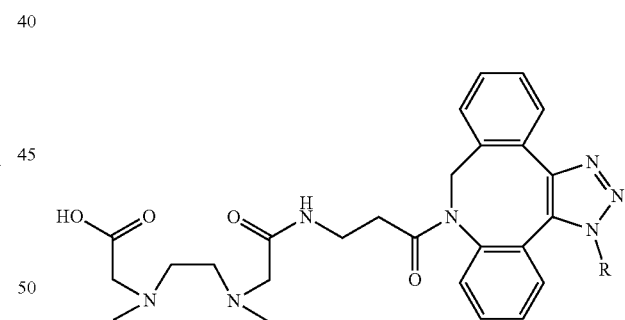
(1-12)
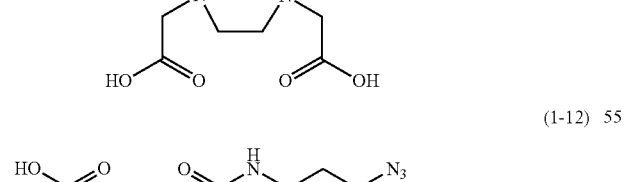
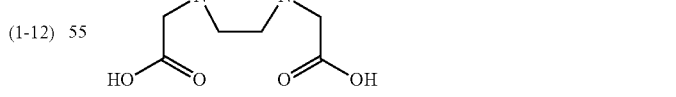
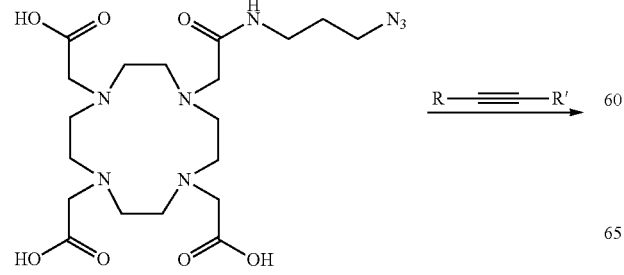
For NOTA represented by General Formula (2), the structures reacted as in Reaction Formulae (2-1) to (2-13) below can be employed. In Reaction Formulae (2-1) to (2-13), represented in order from the left are a NOTA derivative, a substance desired to be bonded (written above the arrow), and a structure after condensation. Reaction Formulae (2-11) to (2-13) are click chemistry-oriented methods of bonding.

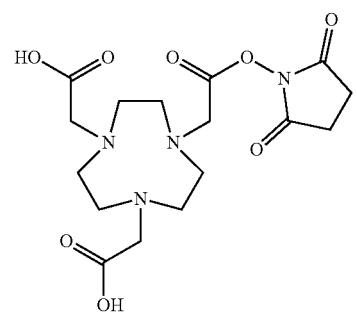 (2-1)
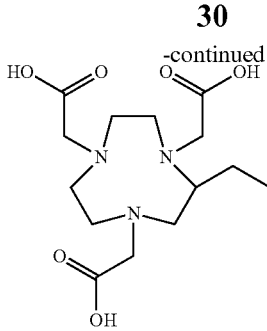 (2-4)
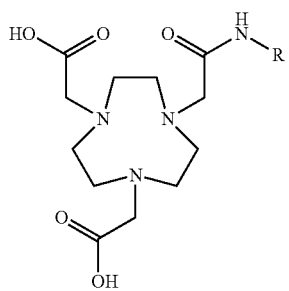
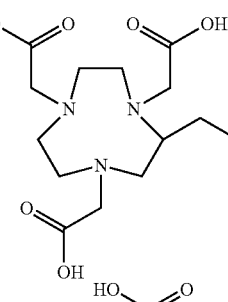
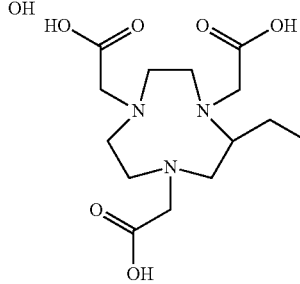 (2-5)
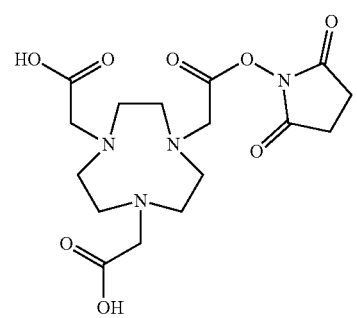 (2-2)
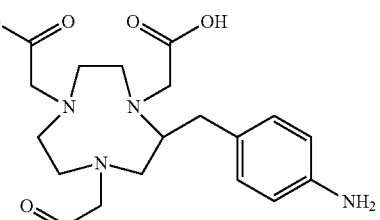
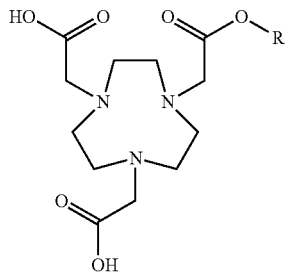
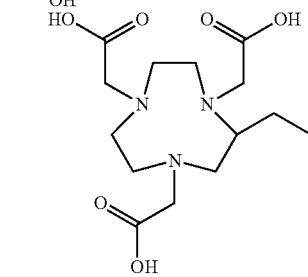 (2-6)
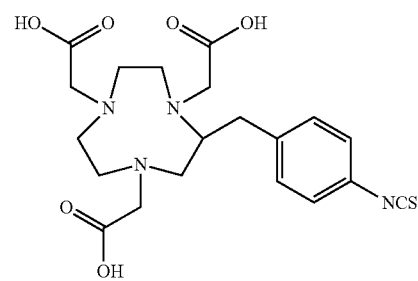 (2-3)
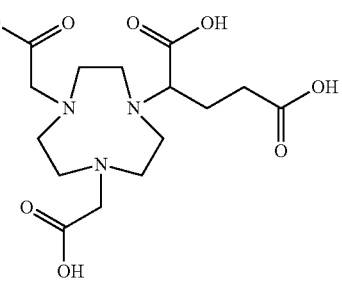

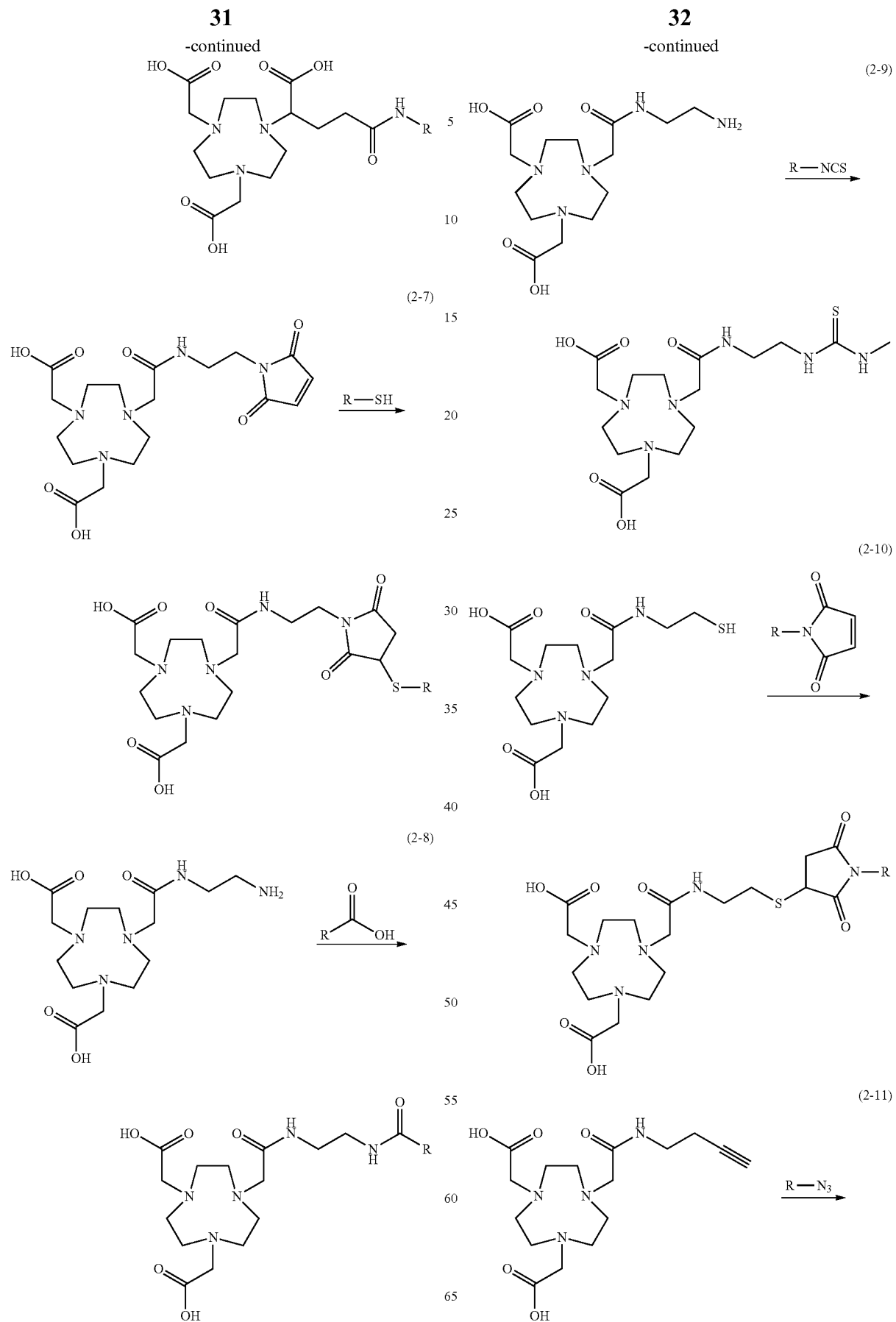

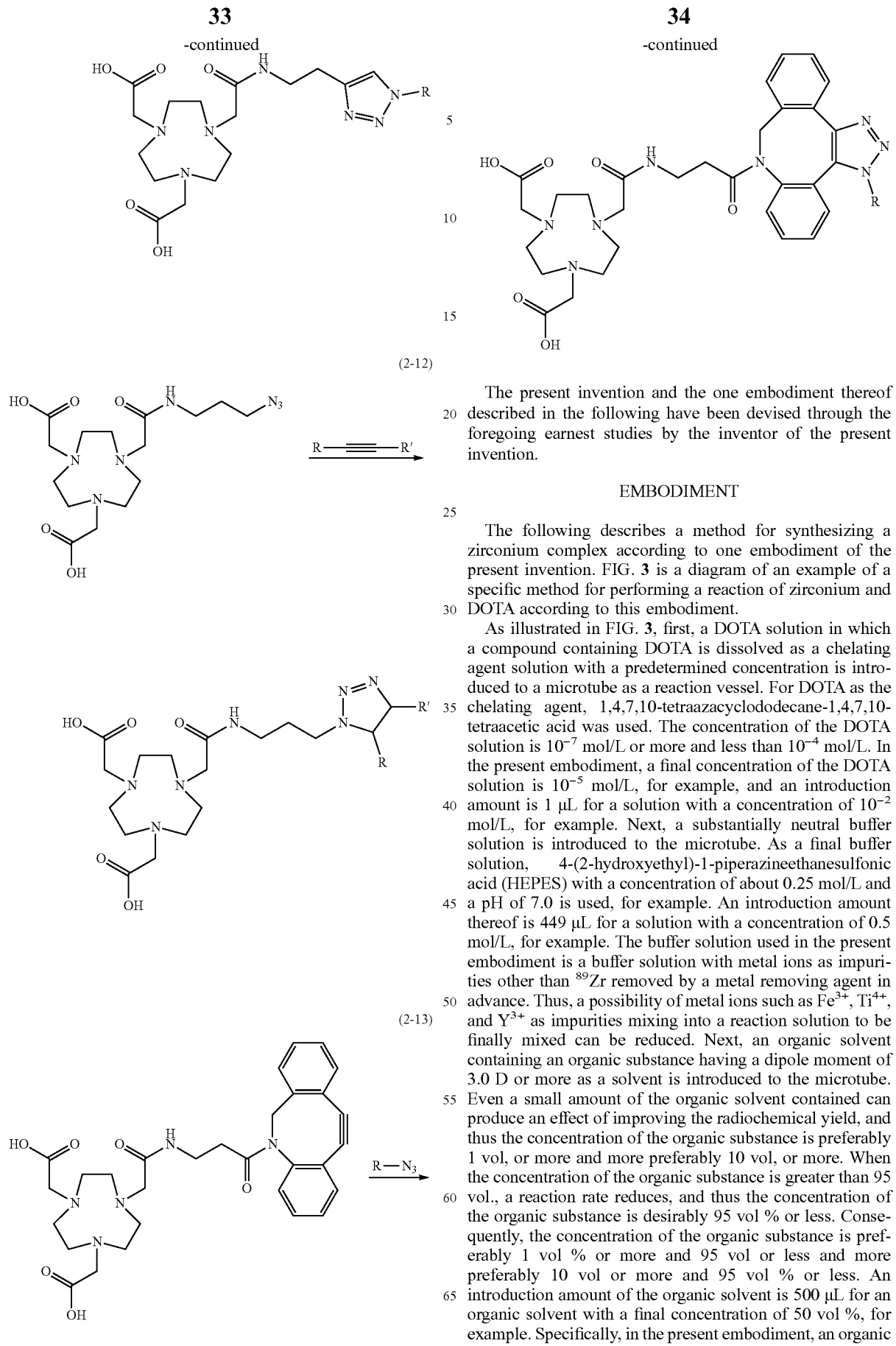

The present invention and the one embodiment thereof described in the following have been devised through the foregoing earnest studies by the inventor of the present invention.

EMBODIMENT

Figure 3:
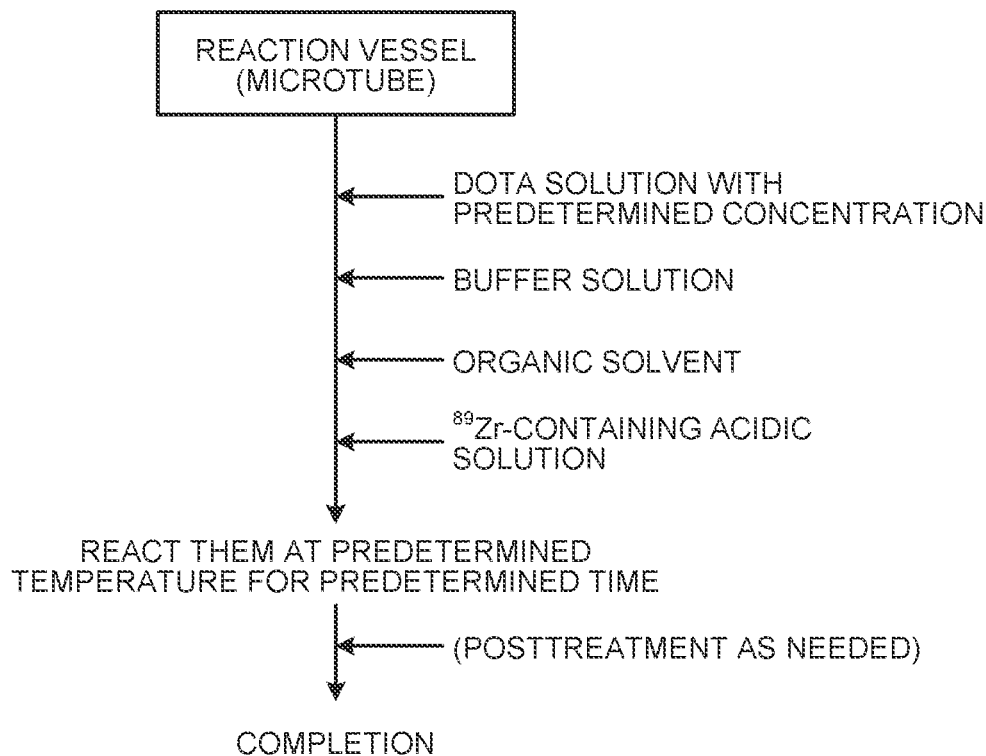
FIG. 3 is a diagram for illustrating an example of a specific method for performing a reaction of zirconium and DOTA according to one embodiment of the present invention.

The following describes a method for synthesizing a zirconium complex according to one embodiment of the present invention. FIG. 3 is a diagram of an example of a specific method for performing a reaction of zirconium and DOTA according to this embodiment.

As illustrated in FIG. 3, first, a DOTA solution in which a compound containing DOTA is dissolved as a chelating agent solution with a predetermined concentration is introduced to a microtube as a reaction vessel. For DOTA as the chelating agent, 1,4,7,10-tetraazacyclododecane-1,4,7,10-tetraacetic acid was used. The concentration of the DOTA solution is $10^{-7}$ mol/L or more and less than $10^{-4}$ mol/L. In the present embodiment, a final concentration of the DOTA solution is $10^{-5}$ mol/L, for example, and an introduction amount is 1 μL for a solution with a concentration of $10^{-2}$ mol/L, for example. Next, a substantially neutral buffer solution is introduced to the microtube. As a final buffer solution, 4-(2-hydroxyethyl)-1-piperazineethanesulfonic acid (HEPES) with a concentration of about 0.25 mol/L and a pH of 7.0 is used, for example. An introduction amount thereof is 449 μL for a solution with a concentration of 0.5 mol/L, for example. The buffer solution used in the present embodiment is a buffer solution with metal ions as impurities other than $^{89}$Zr removed by a metal removing agent in advance. Thus, a possibility of metal ions such as $Fe^{3+}$, $Ti^{4+}$, and $Y^{3+}$ as impurities mixing into a reaction solution to be finally mixed can be reduced. Next, an organic solvent containing an organic substance having a dipole moment of 3.0 D or more as a solvent is introduced to the microtube. Even a small amount of the organic solvent contained can produce an effect of improving the radiochemical yield, and thus the concentration of the organic substance is preferably 1 vol, or more and more preferably 10 vol, or more. When the concentration of the organic substance is greater than 95 vol., a reaction rate reduces, and thus the concentration of the organic substance is desirably 95 vol % or less. Consequently, the concentration of the organic substance is preferably 1 vol % or more and 95 vol or less and more preferably 10 vol % or more and 95 vol % or less. An introduction amount of the organic solvent is 500 μL for an organic solvent with a final concentration of 50 vol %, for example. Specifically, in the present embodiment, an organic solvent containing DMSO having a dipole moment of 3.7 D is used, for example, as the organic solvent, with a final concentration of 50 vol %, for example. The order of introducing the DOTA solution, the buffer solution, and the organic solvent to the microtube is not limited to the order described above, and they can be introduced in various orders.

After the DOTA solution, the buffer solution, and the organic solvent have been introduced to the microtube, an acidic solution containing $^{89}$Zr (a $^{89}$Zr-containing acidic solution) is introduced to the reaction solution within the microtube to generate a mixed solution within the microtube. In the present embodiment, the acidic solution is preferably a solution of a strong acid and is specifically preferably hydrochloric acid (HCl). However, the acidic solution is not necessarily limited to the strong acidic solution such as hydrochloric acid. An introduction amount of the acidic solution containing $^{89}$Zr is 50 μL, for example.

Along with the experiment described above, the inventor of the present invention compared reactivity between a case in which the acidic solution had a concentration of 0.1 mol/L and a case in which it had a concentration of 1 mol/L with the pH of the reaction solution maintained at constant by the buffer solution. Consequently, the inventor of the present invention has found that the $^{89}$Zr-containing acidic solution in which the acidic solution had a concentration of 0.1 mol/L had a higher yield. Specifically, when an organic solvent containing DMSO in an amount of 50 vol % was used, a reaction occurred in both cases in which the concentration of the acidic solution was 0.1 mol/L and 1 mol/L. On the other hand, when an organic solvent containing DMSO in an amount of 10 vol % was used, it was revealed that the reaction rate reduced when the concentration of the acidic solution was 0.1 mol/L. In this regard, Non Patent Literature 2 assumes that the phenomenon in which the reactivity changes is influenced by ionic strength. However, when the inventor of the present invention added sodium chloride (NaCl) to the reaction solution to again measure the reactivity, no change was observed in the reactivity. From this point, the inventor of the present invention assumes that the reason why the reactivity of $^{89}$Zr dissolved in the acidic solution with a concentration of 1 mol/L has higher reactivity than the reactivity of $^{89}$Zr dissolved in the acidic solution with a concentration of 0.1 mol/L is that the chemical form of a $^{89}$Zr ion in water changes by an acid concentration, and that the chemical form in the high concentration acid is suitable for the reaction with DOTA, NOTA, and the like.

After the DOTA solution, the buffer solution, the organic solution, and the $^{89}$Zr-containing acidic solution have been mixed together in the microtube, the mixed solution is heated at a predetermined temperature and is maintained for a predetermined time. Thus, DOTA and $^{89}$Zr react. In the present embodiment, the $^{89}$Zr-containing acidic solution is preferably introduced to the microtube immediately before the heating of the mixed solution; this is because even in the presence of the organic solvent such as DMSO, when being left under a neutral condition and at room temperature, $^{89}$Zr experiences hydroxidation to become inactive in the reaction with DOTA. Even if temperature is raised thereafter, the reaction of $^{89}$Zr and DOTA does not proceed. It is assumed that this is because while the reaction with DOTA requires relatively high activation energy, hydroxidation has low activation energy. Thus, after $^{89}$Zr is added, the mixed solution is preferably immediately heated to the predetermined temperature to immediately be reacted with DOTA. After $^{89}$Zr has formed a complex with DOTA, 89Zr does not experience hydroxidation. Thus, $^{89}$Zr and DOTA are reacted without being influenced by impurities, and thus the reaction can efficiently be performed. In the present embodiment, the predetermined temperature is preferably 35° C. or more; if the substance bonding to DOTA is a substance resistant to high temperature, the predetermined temperature may be 90° C. or more, for example, and specifically 95° C., for example. The predetermined time is about 30 minutes, for example. Thus, the reaction of $^{89}$Zr and DOTA according to Reaction Formula (401) below ends, and a zirconium complex in which DOTA bonds to $^{89}$Zr is obtained.

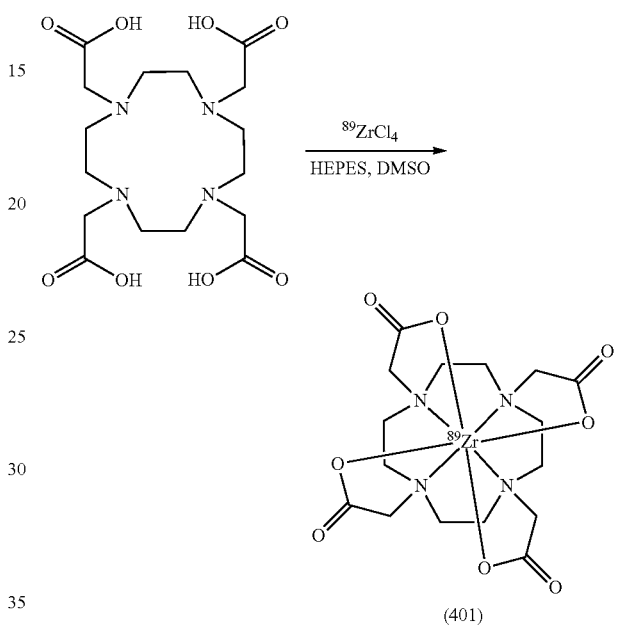

(401)

The acidic solution containing $^{89}$Zr is strongly acidic, and when it is added to the reaction vessel, there is a possibility of pH significantly changing. For this reason, even after the $^{89}$Zr-containing acidic solution is added to the microtube using a high concentration buffer solution, adjustment is required so as to cause the range of pH to fall under a desired range. That is, after the $^{89}$Zr-containing acidic solution is added, pH is preferably checked using a pH meter, pH test paper, or the like. When a basic solution is added after the $^{89}$Zr-containing acidic solution is added to the microtube, there is a possibility that $^{89}$Zr will experience hydroxidation in a short time to become inactive in the reaction with DOTA, and thus work of neutralization using the basic solution is preferably avoided. The range of pH is preferably 4 or more and 9 or less, more preferably 5 or more and 9 or less, and even more preferably 6 or more and 8 or less.

After the complex forming reaction of DOTA and $^{89}$Zr, posttreatment is performed as needed. DMSO and the buffer solution are removed to be replaced by a physiological saline solution or an ethanol-physiological saline solution mixed solution, for example. Examples of methods include solid phase extraction using an ion exchange resin, a C18 column, or a graphite carbon column, high performance liquid chromatography (HPLC) using a liquid chromatography apparatus, and separation; a method suitable for each drug is employed.

COMPARATIVE EXAMPLE

Figure 4:
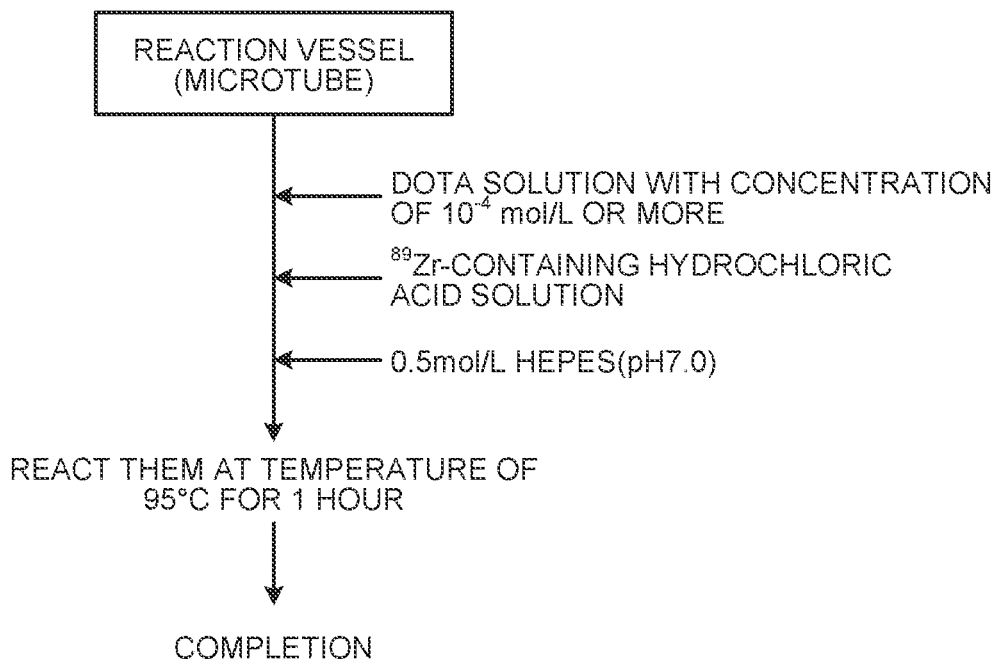
FIG. 4 is a diagram for illustrating a specific method for performing a reaction of zirconium and DOTA according to a conventional technology as a comparative example.

To compare with the foregoing embodiment, the following describes a method for synthesizing a zirconium complex according to a conventional technology as a comparative example. FIG. 4 is a diagram of a specific method for performing a reaction of zirconium and DOTA according to the conventional technology.

As illustrated in FIG. 4, first, a DOTA solution with a concentration of $10^{-4}$ mol/L or more is introduced to a microtube as a reaction vessel. Next, the $^{89}$Zr-containing acidic solution is introduced to the microtube. Next, HEPES with a pH of 7.0 as a substantially neutral buffer solution is introduced to the microtube. Subsequently, they are reacted at a temperature of 95° C., which is 90° C. or more, for about 1 hour to react DOTA and $^{89}$Zr in accordance with Reaction Formula (402) below. Thus, a zirconium complex in which DOTA bonds to $^{89}$Zr is obtained.

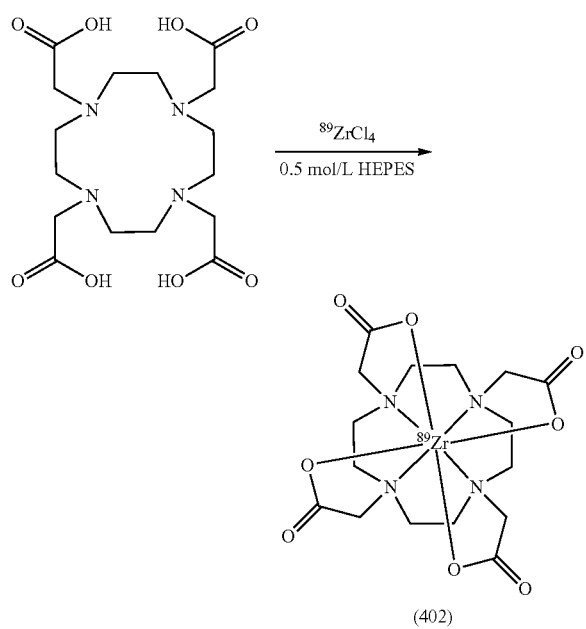

(402)

When the zirconium complex is generated by the method for synthesizing a zirconium complex according to the comparative example, it was confirmed that 90% or more of the dissolved $^{89}$Zr adhered to the microtube. It was confirmed that about 95% of $^{89}$Zr dissolved in the reaction solution other than $^{89}$Zr adhering to the microtube reacted. That is, it is revealed that in the comparative example, the radiochemical yield is about ((1−0.9)×0.95×100=) 9.5% with respect to the original amount of $^{89}$Zr. On the other hand, when the zirconium complex is generated by the method for synthesizing a zirconium complex by the one embodiment described above, it was confirmed that $^{89}$Zr adhering to the microtube was about 9% of the dissolved $^{89}$Zr. Furthermore, it was confirmed that about 951 of $^{89}$Zr dissolved in the reaction solution other than $^{89}$Zr adhering to the microtube reacted. That is, the radiochemical yield is about ((1−0.09)×0.95×100=) 86.5% with respect to the original amount of $^{89}$Zr, which reveals that the radiochemical yield about nine times that of the comparative example can be ensured. In addition, it is revealed that the reaction proceeds in a short reaction time even with a low concentration of DOTA.

As described in the foregoing, the one embodiment of the present invention can synthesize a zirconium complex by reacting DOTA, even with a low concentration of about $10^{-7}$ to $10^{-4}$ mol/L, and $^{89}$Zr with a high reaction rate of 90% or more.

One embodiment of the present invention has specifically been described; the present invention is not limited to the one embodiment described above and allows various modifications based on the technical thought of the present invention. One formed by combining the components described above as appropriate is also included in the present invention. Further effects and modifications can be derived easily by those skilled in the art. Consequently, wider aspects of the present invention are not limited to the embodiment described above and allows various modifications. The values and materials described in the one embodiment described above, for example, are only by way of example; values and materials different therefrom may be used as needed, and the present invention is not limited by the descriptions and the drawings forming part of the disclosure of the present invention by the present embodiment.

Although in the one embodiment described above hydrochloric acid (HCl) is used as the acidic solution, for example, another acidic solution can also be used. Although in the one embodiment described above DMSO is used as the solvent containing an organic substance having a dipole moment of 3.0 D or more, it is not necessarily limited to DMSO; an aqueous solution of N,N-dimethylformamide (DMF), N-methylformamide (NMF), N-methylpyrrolidone (NMP), formamide (FA), urea, or guanidine can also be used.

INDUSTRIAL APPLICABILITY

The method for synthesizing a zirconium complex according to the present invention can suitably be used for medical imaging.

The invention claimed is:

1. A method for synthesizing a zirconium complex comprising:

mixing
  a solvent containing an organic substance having a dipole moment of 3.0 D or more,
  a chelating agent solution in which a chelating agent containing a structure represented by General Formula (1) or General Formula (2) is dissolved, and
  zirconium dissolved in an acidic solution, to obtain a mixed solution; and
setting the mixed solution at a predetermined temperature or more to synthesize a zirconium complex,
wherein a concentration of the organic substance is 50 vol % or more and 95 vol % or less,

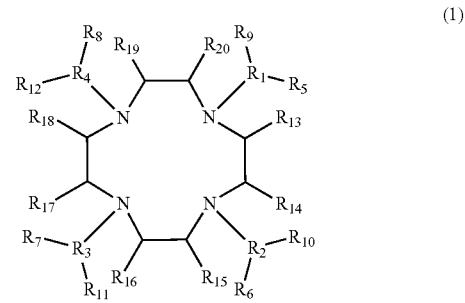

(1)

-continued

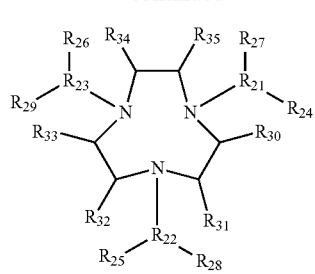
(2)

wherein in General Formula (1):

$R_1$, $R_2$, $R_3$, and $R_4$ being each a hydrogen (—H) (in this case, none of $R_5$ to $R_{12}$ is further connected), a —CH— group, —(CH$_2$),CH— group, a —C(=O) (CH$_2$),CH— group, or a —(CH$_2$) C(=O)N-group;

n being an integer of 0 or more;

at least two of $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ being at least two selected from a carboxylic acid, a primary amide, hydroxamic acid, phosphonic acid, phosphoric acid, sulfonic acid, an alcohol, an amine, phenol, aniline, and an ester, a secondary amide, and a phosphate that are each obtained by adding a substituent to the aforementioned, with the residual substituents being each a hydrogen, an alkyl chain, a tert-butyl blocked carboxylic acid, nitrobenzene, or a substituent-added alkyl chain;

a positron emission tomography (PET) probe or a functional group facilitating bonding of a PET probe being optionally added to a functional group contained in $R_5$ to $R_{20}$;

the functional group facilitating bonding being a carboxylic acid, a succinimide carboxylate, a tetrafluorophenol carboxylate, an alcohol, an amine, a thiol, isothiocyanate, maleimide, phenol, aniline, benzoic acid, phenyl isothiocyanate, or an alkyne, an azide, dibenzocyclooctyne (DBCO), bicyclononyne (BCN), trans-cyclooctene (TCO), norbornene, tetrazine, or methyltetrazine, which are each a click chemistry reagent; and $R_1$ to $R_{20}$ optionally having a structure of the functional group facilitating bonding or a condensed structure of a PET probe and the functional group facilitating bonding, and wherein in General Formula (2):

$R_{21}$, $R_{22}$, and $R_{23}$ being each a hydrogen (—H) (in this case, none of $R_{24}$ to $R_{29}$ is further connected), a —CH— group, —(CH$_2$),CH— group, a —C(=O) (CH$_2$),CH— group, or a —(CH$_2$) C(=O)N-group;

n being an integer of 0 or more;

at least two of $R_{24}$, $R_{25}$, $R_{26}$, $R_{27}$, $R_{28}$, $R_{29}$, $R_{30}$, $R_{31}$, $R_{32}$, $R_{33}$, $R_{34}$, and $R_{35}$ being at least two selected from a carboxylic acid, a primary amide, hydroxamic acid, phosphonic acid, phosphoric acid, sulfonic acid, an alcohol, an amine, phenol, aniline, and an ester, a secondary amide, and a phosphate that are each obtained by adding a substituent to the aforementioned, with the residual substituents being each a hydrogen, an alkyl chain, a tert-butyl blocked carboxylic acid, nitrobenzene, or a substituent-added alkyl chain;

a PET probe or a functional group facilitating bonding of a PET probe being optionally added to a functional group contained in $R_{24}$ to $R_{35}$;

the functional group facilitating bonding being the following functional group, a carboxylic acid, a succinimide carboxylate, a tetrafluorophenol carboxylate, an alcohol, an amine, a thiol, isothiocyanate, maleimide, phenol, aniline, benzoic acid, phenyl isothiocyanate, or an alkyne, an azide, DBCO, BCN, TCO, norbornene, tetrazine, or methyltetrazine, which are each a click chemistry reagent; and $R_{24}$ to $R_{35}$ optionally having a structure of the functional group facilitating bonding or a condensed structure of a PET probe and the functional group facilitating bonding, and wherein the organic substance is at least one substance selected from the group consisting of dimethylsulfoxide (DMSO), N,N-dimethylformamide (DMF), N-methylformamide (NMF), N-methylpyrrolidone (NMP), and urea.

2. The method for synthesizing a zirconium complex according to claim 1, wherein the predetermined temperature is 35° C. or more.

3. The method for synthesizing a zirconium complex according to claim 1, wherein the solvent is a solvent purified with a metal removing agent.

4. The method for synthesizing a zirconium complex according to claim 1, wherein the acidic solution is hydrochloric acid.

5. The method for synthesizing a zirconium complex according to claim 1, wherein zirconium dissolved in the acidic solution is mixed into a solution in which the solvent and the chelating agent solution are mixed together before heating at the predetermined temperature or more or after the heating.

6. The method for synthesizing a zirconium complex according to claim 1, wherein at least one of $R_5$ to $R_{20}$ in General Formula (1) or at least one of $R_{24}$ to $R_{35}$ in General Formula (2) bonds a molecular probe or bonds a linker to a molecular probe, via at least one structure selected from the group consisting of Chemical Formulae (16) to (21) and (26) as shown below:

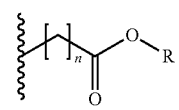
(16)

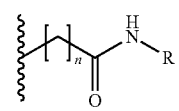
(17)

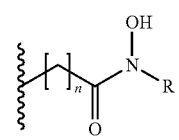
(18)

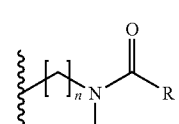
(19)

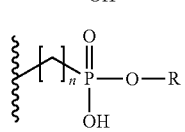
(20)

-continued

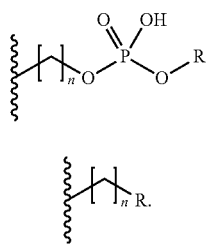

(21)

(26)

7. The method for synthesizing a zirconium complex according to claim 6, wherein the molecular probe is a protein or a peptide.

8. The method for synthesizing a zirconium complex according to claim 7, wherein the protein or the peptide includes a natural amino acid, a non-natural amino acid, or both the natural amino acid and the non-natural amino acid and has a linear-chain structure or a cyclic structure.

9. The method for synthesizing a zirconium complex according to claim 6, wherein the linker is polyethylene glycol, an alkyl chain, piperazine, or a complex thereof.

10. The method for synthesizing a zirconium complex according to claim 7, wherein the linker is polyethylene glycol, an alkyl chain, piperazine, or a complex thereof.

11. The method for synthesizing a zirconium complex according to claim 1, wherein oxalic acid is added to the acidic solution to adjust a concentration of the oxalic acid to be $10^{-6}$ mol/L or more and less than $10^{-4}$ mol/L.

12. The method for synthesizing a zirconium complex according to claim 1, wherein at least one of $R_{13}$, $R_{14}$, $R_{15}$, $R_{16}$, $R_{17}$, $R_{18}$, $R_{19}$, and $R_{20}$ is at least one selected from a carboxylic acid, a primary amide, hydroxamic acid, phosphonic acid, phosphoric acid, sulfonic acid, an alcohol, an amine, phenol, aniline, and an ester, a secondary amide, and a phosphate that are each obtained by adding a substituent to the aforementioned, with the residual substituents being each a hydrogen, an alkyl chain, a tert-butyl blocked carboxylic acid, nitrobenzene, or a substituent-added alkyl chain.

\* \* \* \* \*